United States Patent
Verzal et al.

(10) Patent No.: US 11,806,542 B2
(45) Date of Patent: Nov. 7, 2023

(54) FEEDTHROUGH MOUNTING FOR AN ELECTRONIC DEVICE, SUCH AS AN IMPLANTABLE MEDICAL DEVICE, AND METHODS OF MAKING THE SAME

(71) Applicant: INSPIRE MEDICAL SYSTEMS, INC., Golden Valley, MN (US)

(72) Inventors: Kevin Verzal, Lino Lakes, MN (US); Lily Berger, St. Louis Park, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 140 days.

(21) Appl. No.: 17/172,786

(22) Filed: Feb. 10, 2021

(65) Prior Publication Data

US 2021/0244954 A1    Aug. 12, 2021

Related U.S. Application Data

(60) Provisional application No. 62/972,862, filed on Feb. 11, 2020.

(51) Int. Cl.
*A61N 1/375* (2006.01)

(52) U.S. Cl.
CPC ......... *A61N 1/3754* (2013.01); *A61N 1/3758* (2013.01)

(58) Field of Classification Search
CPC ........................... A61N 1/3754; A61N 1/3758
See application file for complete search history.

(56) References Cited

U.S. PATENT DOCUMENTS

| | | |
|---|---|---|
| 5,870,272 A | 2/1999 | Seifried et al. |
| 6,414,835 B1 | 7/2002 | Wolf et al. |
| 8,536,468 B2 | 9/2013 | Teske |
| 2002/0027484 A1 | 3/2002 | Stevenson et al. |
| 2003/0179536 A1* | 9/2003 | Stevenson ................ H01G 4/35 361/302 |
| 2007/0112398 A1 | 5/2007 | Stevenson et al. |
| 2011/0232961 A1* | 9/2011 | Teske ................... A61N 1/3754 174/650 |
| 2018/0015290 A1 | 1/2018 | Deininger et al. |

FOREIGN PATENT DOCUMENTS

| | | |
|---|---|---|
| EP | 2371418 A2 | 10/2011 |
| WO | 03073450 A1 | 9/2003 |

* cited by examiner

*Primary Examiner* — Eugene T Wu
(74) *Attorney, Agent, or Firm* — Dicke, Billig & Czaja, PLLC

(57) ABSTRACT

Solder reflowing a feedthrough pin to internal electronics of an electronic device and interface block constructions conducive to solder reflow.

17 Claims, 20 Drawing Sheets

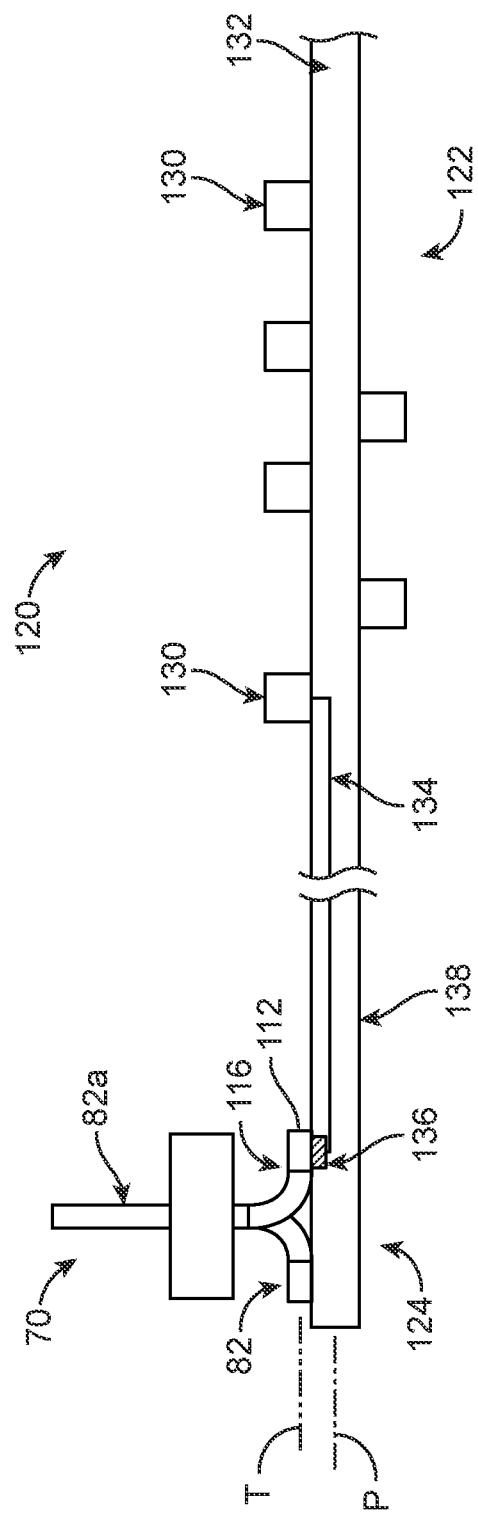

FEEDTHROUGH MOUNTING FOR AN ELECTRONIC DEVICE, SUCH AS AN IMPLANTABLE MEDICAL DEVICE, AND METHODS OF MAKING THE SAME

CROSS-REFERENCE TO RELATED APPLICATIONS

This application claims the benefit of the filing date of U.S. Provisional Application Ser. No. 62/972,862, filed Feb. 11, 2020 and entitled "Feedthrough Mounting for an Electronic Device, Such as an Implantable Medical Device, and Methods of Making the Same," the entire teachings of which are incorporated herein by reference.

BACKGROUND

Many patients benefit from therapy provided by an implantable medical device including a feedthrough pin connected to enclosed circuitry. With these and other implantable medical device therapy applications, manufacture of the implantable medical device can be improved with reference to the feedthrough pin construction.

BRIEF DESCRIPTION OF THE DRAWINGS

FIGS. 5A and 5B are side views illustrating mounting of feedthrough pins of the interface block of FIG. 3A to a printed circuit board assembly in accordance with methods of the present disclosure.

DETAILED DESCRIPTION

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense. It is to be understood that features of the various examples described herein may be combined, in part or whole, with each other, unless specifically noted otherwise.

At least some examples of the present disclosure are directed to systems and devices for diagnosis, therapy and/or other care of medical conditions. At least some examples may comprise implantable devices and/or methods comprising use of implantable devices.

At least some examples of present disclosure are directed to feedthrough pin constructions for hermetically sealed-type electrical devices, and methods of mounting or bonding a feedthrough pin to internal electronics of such devices. In some embodiments, the methods of mounting or bonding a feedthrough pin to internal electronics utilize solder reflow, for example solder reflow/surface mount technology often employed for printed circuit board assembly (PCBA) bonding. The feedthrough pin and corresponding interface block or header constructions of the present disclosure are uniquely conducive to solder reflow bonding of the feedthrough pin(s) to internal electronics. In some non-limiting embodiments, the devices, systems and methods of the present disclosure provide an implantable medical device, such as an implantable pulse generator assembly useful, for example, as part of an implantable medical device for sleep disordered breathing (SDB) therapy, such as obstructive sleep apnea (OSA) therapy, which may comprises monitoring, diagnosis, and/or stimulation therapy. However, in other examples, the devices incorporating the interface blocks (and corresponding methods of reflow soldering a feedthrough pin to internal electronics) is used for other types of therapy, including, but not limited to, other types of neurostimulation or cardiac therapy. In some embodiments, such other implementations include therapies, such as but not limited to, central sleep apnea, complex sleep apnea, cardiac disorders, pain management, seizures, deep brain stimulation, and respiratory disorders. Other devices utilizing feedthrough pins to hermetically sealed electronics can equally benefit from the present disclosure. For example, the present disclosure can be beneficial with aerospace or military devices/applications that incorporate feedthrough pins to electronics in a hermetic sealed enclosure.

Figure 1:
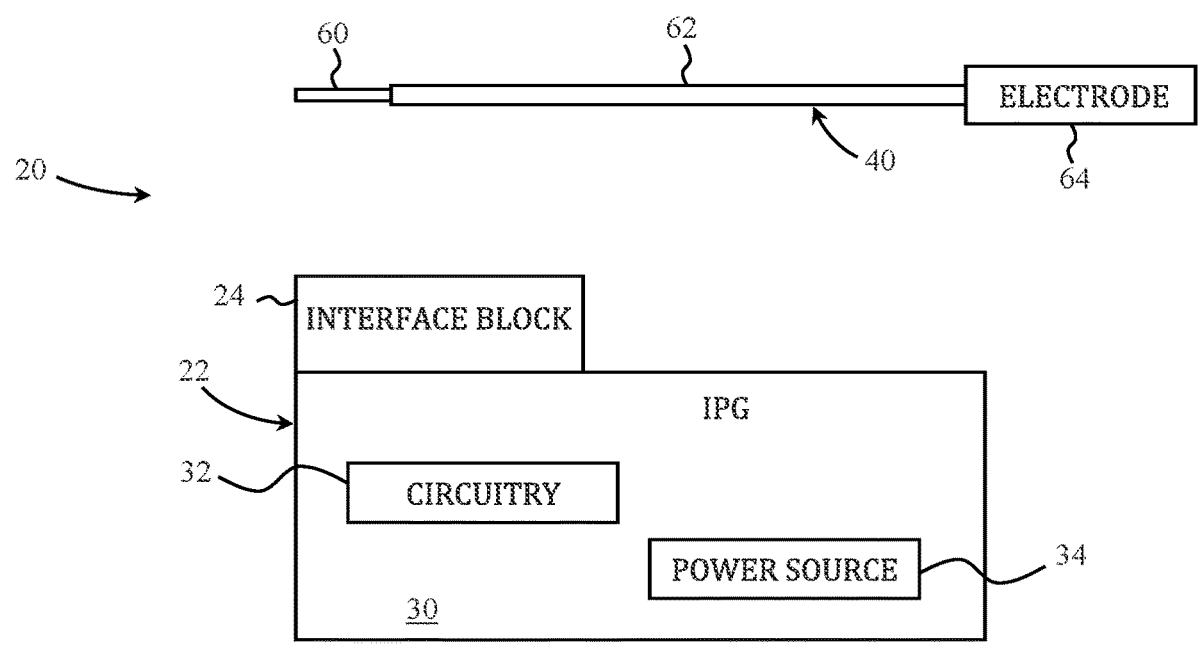
FIG. 1 is a block diagram schematically illustrating an interface block of the present disclosure as part of an electronic device, for example an implantable medical device.

FIG. 1 is a block diagram schematically representing one example of an implantable medical device (IMD) 20 in accordance with principles of the present disclosure. The IMD 20 can include an implantable pulse generator (IPG) assembly 22 and an interface block 24. The IPG assembly 22 can include a housing 30 containing circuitry 32 and a power source 34 (e.g., battery). The housing 30 is configured to render the IPG assembly 22 appropriate for implantation into a human body, and can incorporate biocompatible materials and hermetic seal(s). The circuitry 32 can include circuitry components and wiring apparent to one of ordinary skill appropriate for generating desired stimulation signals (e.g., converting energy provided by the power source 34 into a desired stimulation signal), for example in the form of a stimulation engine. The IPG assembly 22 may comprise an IPG for treating sleep disordered breathing (SDB), such as but not limited to obstructive sleep apnea. In some examples, the IPG assembly 22 may comprise an IPG for treating other diseases, physiologic conditions, etc.

In general terms, the interface block 24 is configured to receive (e.g., removably receive) one or more electrical components (e.g., leads, antenna, etc.), as sometimes referred to as a "header", and to provide for electrical connection between such components and the circuitry 32 within the housing 30, as sometime referred to as a "feedthru electrical interface". For example, with the non-limiting embodiment of FIG. 1, the interface block 24 can be configured to establish an electrical connection with an implantable stimulation lead 40. Regardless, and with reference to FIG. 2A, the interface block 24 includes a support body 50 carrying one or more feedthrough pins 52. Each feedthrough pin 52 is formed of an electrically conductive material, and extends between opposing, first and second ends 54, 56 (labeled for one of the pins 52 in FIG. 2A). The first end 54 is available for electrical connection with an electrical component external the housing 30. Upon final assembly (FIG. 2B), the second end 56 is disposed within the housing 30 and is electrically coupled to the circuitry 32. The first end 54 is located external the housing 30. One or more ground pins 58 can also be provided in some embodiments. Where provided, the ground pin 58 is akin to the feedthrough pins 52, projecting into the housing 30 upon final assembly for electrical connection to a ground component of the circuitry 32. The ground pin 58 is further coupled to a neutral or ground surface of the interface block 24. While some embodiments of the present disclosure incorporate the interface block 24 as part of an IMD, in other embodiments the interface blocks (and corresponding methods of bonding feedthrough pins to internal electronics) of the present disclosure can be employed with a plethora of other electronic devices that may or may not be intended for medical use or implantation into a human body.

The support body 50 can assume various forms appropriate for a desired end use. In some embodiments, the support body 50 can be, or can be akin to, a case or housing that encloses at least the first end 54 of each of the feedthrough pins 52 and defines a port or opening through which a connector end of the electrical component(s) of interest can be inserted into the case and electrically coupled to the feedthrough pin(s) 52 (e.g., a connector end 60 of the stimulation lead 40 shown in FIG. 1). In other embodiments, the support body 50 can have a more open construction. Regardless, upon final assembly to the housing 30 of the IPG assembly 22, the support body 50 is configured to complete or maintain a seal, for example a hermetic seal, with respect to the housing 30. As described in greater detail below, in some embodiments a format of the feedthrough pin(s) 52 (and the optional ground pin 58) and/or other components provided with the IPG assembly 22 is conducive to solder reflow electrical bonding or coupling of the feedthrough pin(s) 52 with the circuitry 32.

Figure 3A:
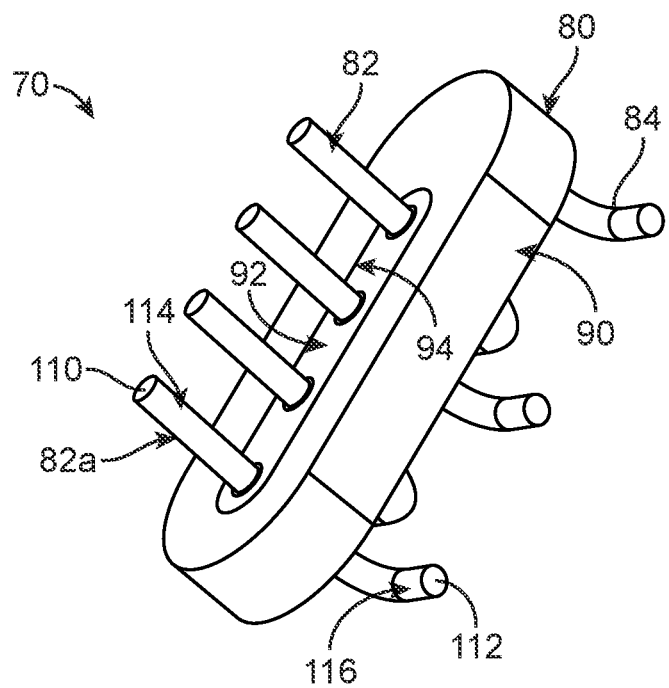
FIG. 3A is a top perspective view of an interface block in accordance with principles of the present disclosure and useful, for example, as the interface block of FIG. 1 or as sub-assembly of the interface block of FIG. 1.
Figure 3B:
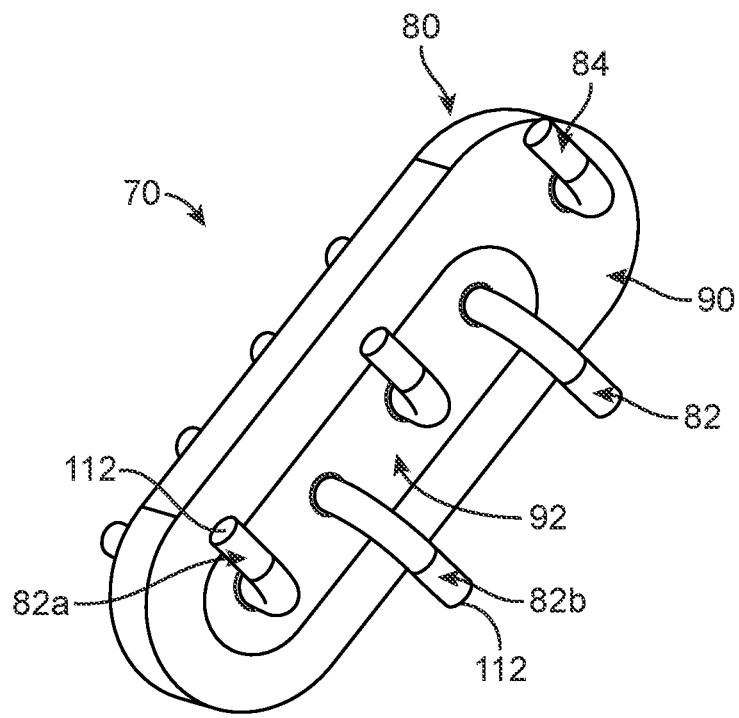
FIG. 3B is a bottom perspective view of the interface block of FIG. 3A.

One non-limiting example of an interface block 70 in accordance with principles of the present disclosure and useful as, or as a sub-assembly of, the interface block 24 (FIG. 1) is provided in FIGS. 3A and 3B. The interface block 70 includes a flange assembly 80, one or more feedthrough pins 82, and an optional ground pin 84. The flange assembly 80 maintains the pins 82, 84, and is generally configured for mounting (e.g., hermetically sealed mounting) to the IPG assembly housing 30 (FIG. 1). The flange assembly 80 can include a flange body 90 and an insulator body 92. The flange body 90 is sized and shaped for mounting (e.g., welding) to a correspondingly-sized opening in the IPG assembly housing 30 (FIG. 1), and defines passage 94 therethrough. The insulator body 92 is sized and shaped for assembly within the passage 94, and can be formed of an electrically non-conductive material (e.g., ceramic). In other embodiments, the flange assembly 80 need not include a discernable flange body apart from the insulator body 92. With these and similar embodiments, the insulator body 92 is hermetically joined directly to the housing 30 (with the housing 30 providing or carrying a component akin to the flange body 90 to which the insulator body 92 is directly assembled). With any of the embodiments of the present disclosure, then, the "flange assembly" (e.g., the flange assembly 80) can consist solely of the insulator body 92, and need not include the flange body 90.

Figure 3C:
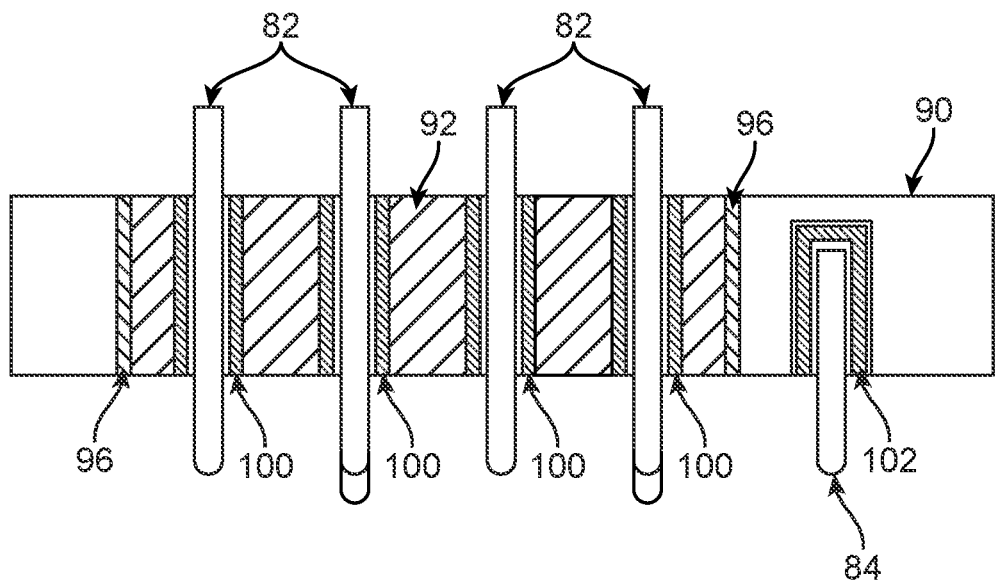
FIG. 3C is a side cross-sectional view of the interface block of FIG. 3A.
Figure 3D:
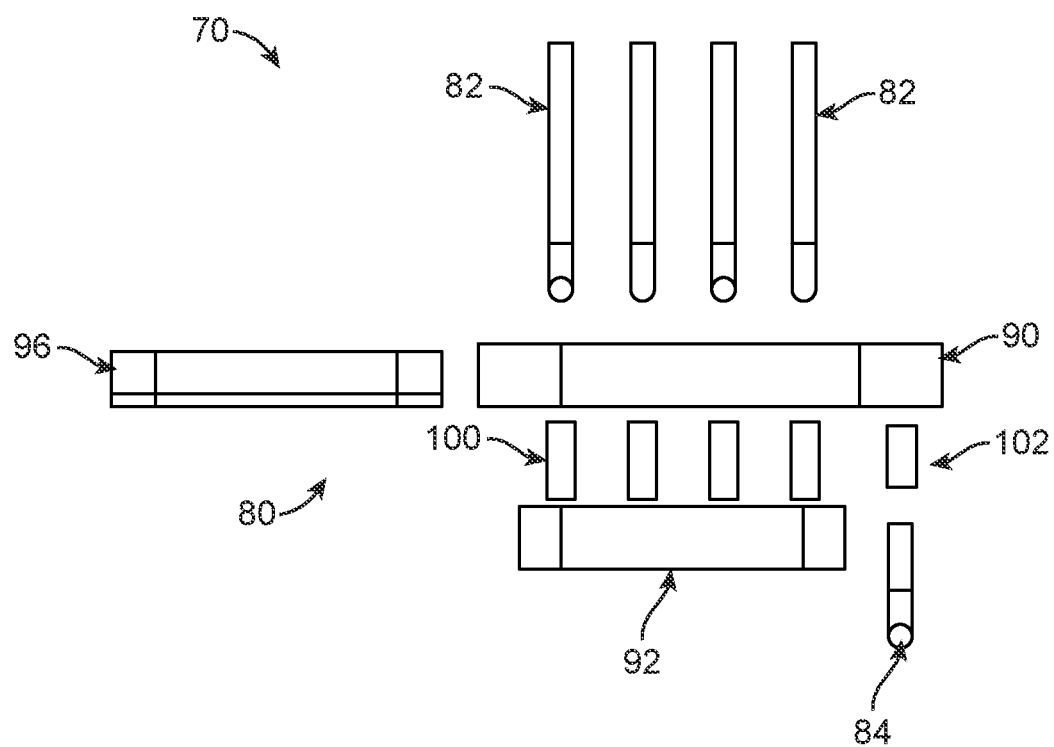
FIG. 3D is an exploded view of the interface block of FIG. 3A.

With additional reference to FIGS. 3C and 3D, the insulator body 92 can be secured to the flange body 90 in various manners known in the art. For example, a joining material 96 can be employed to affix the insulator body 92 to the flange body 90. A composition of the joining material 96 can be selected to fasten to the otherwise disparate materials of both the flange body 90 and the insulator body 92 (e.g., brazed gold, glass). Regardless, the insulator body 92 defines one or more apertures 98 (one of which is labeled in FIG. 3C) each sized to receive a corresponding one of the feedthrough pins 82. The feedthrough pin(s) 82 can be affixed to the insulator body 92 via an appropriate joining material 100 (e.g., brazed gold, glass). Finally, where provided, the ground pin 84 can be secured to the flange body 90 via an appropriate joining material 102 (e.g., brazed gold, glass).

A construction and/or format of the interface block 70 can assume various other forms as is known in the art. For example, the flange body 90 can have a wide variety of other shapes, and can be connected to the insulator body 92 in a number of different manners. Regardless, each of the feedthrough pins 82 can be viewed as defining or extending between opposing, first and second terminal ends 110, 112 (labeled in FIG. 3A for a first one of the feedthrough pins 82a). With additional reference to FIG. 4A, a shape of the feedthrough pin 82a defines a leading region 114 extending from and including the first end 110, and an opposing trailing region 116 extending from and including the second end 112. The leading and trailing regions 114, 116, and thus the first and second ends 110, 112 are located or disposed at opposite sides of the flange assembly 80. As a point of reference, the cross-sectional view of FIG. 4B represents, in simplified form, an arrangement of the interface block 70 relative to an assembly housing 30 (drawn in phantom). The interface block 70 is configured such that upon final assembly of the flange body 90 to the housing 30 (or, in other embodiments, of the insulator body 92 directly to the housing 30), the first end 110 is located external the housing 30, whereas the second end 112 is disposed internally within the housing 30. Thus, the feedthrough pin 82a extends between the sealed (e.g., hermetically sealed) interior of the housing 30 and an environment exterior the housing 30.

Figure 4A:
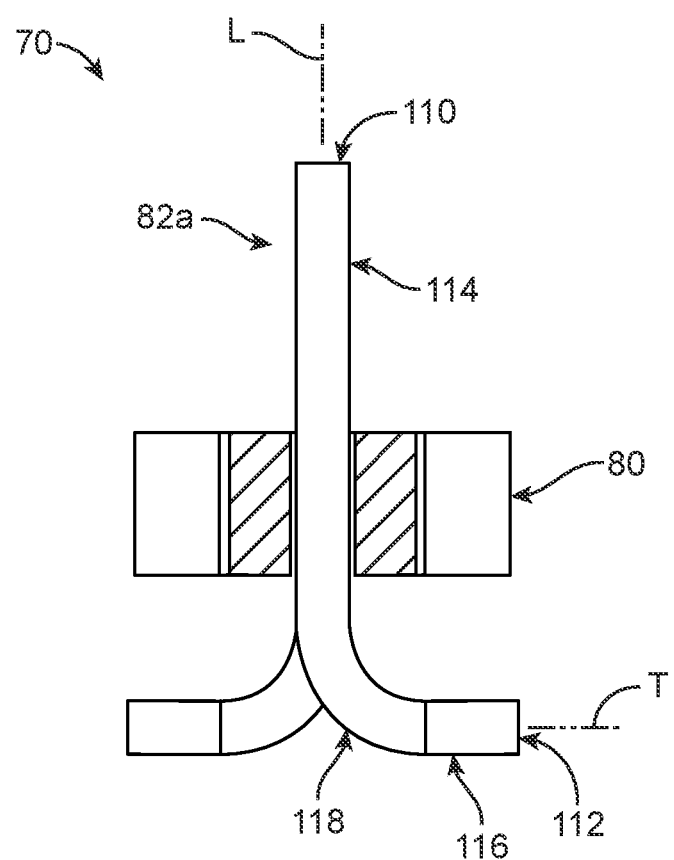
FIG. 4A is an end cross-sectional view of the interface block of FIG. 3A.
Figure 4B:
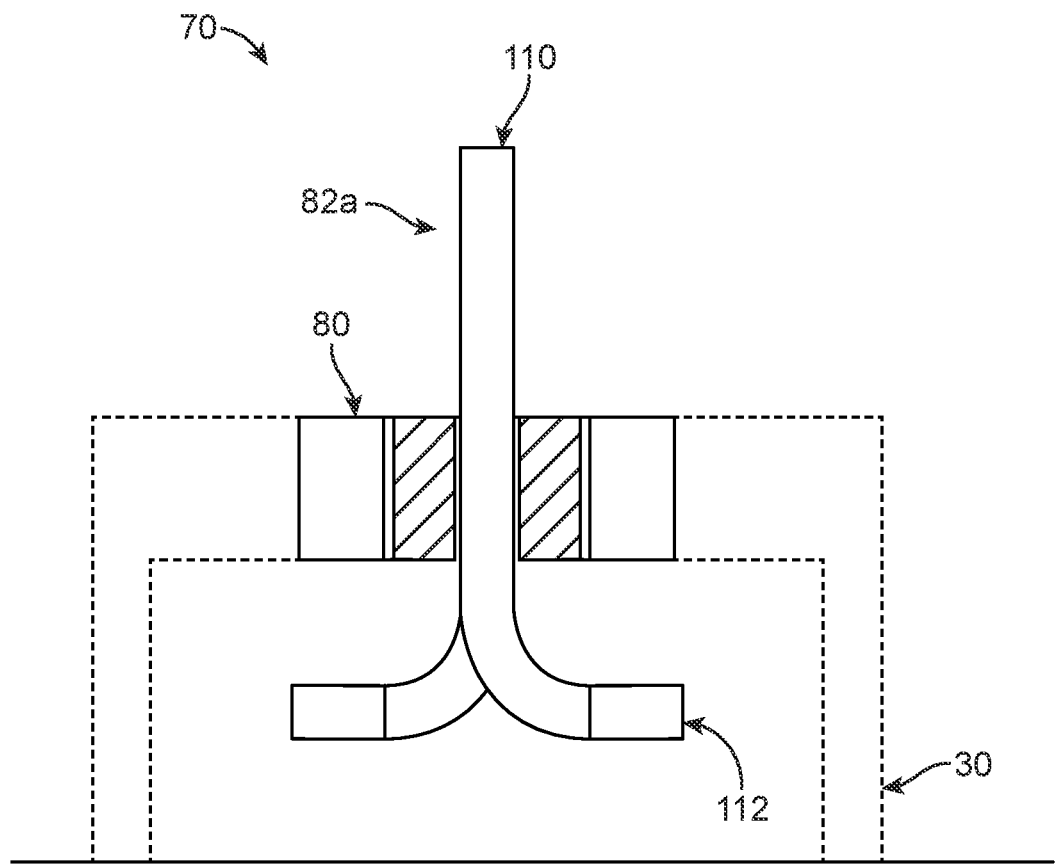
FIG. 4B schematically illustrates assembly of the interface block of FIG. 4A to a housing of an electronic device.

With the non-limiting example of FIG. 4A, a shape of the feedthrough pin 82a further defines an intermediate region 118 extending between the leading and trailing regions 114, 116. In some embodiments, the intermediate region 118 forms a bend along a longitudinal length thereof, generating a change in a spatial arrangement of a central axis of the feedthrough pin 82a. For example, the leading region 114 can be viewed as being linear or straight, defining a leading region central axis L; similarly, the trailing region 116 can be viewed as being linear or straight, defining a trailing region central axis T. A curvature or bend along the intermediate region 118 is such that the leading region central axis L is non-parallel with the trailing region central axis T. For example, a bend in the range of 70-110 degrees can be defined along the intermediate region 118 such that the leading region central axis L and the trailing region central axis T combine to define an angle in the range of 70-110 degrees. In related examples, the leading region central axis L and the trailing region central axis T are substantially perpendicular (i.e., within 5 degrees of a truly perpendicular relationship).

Returning to FIGS. 3A and 3B, one or more or all of the feedthrough pins 82 can have the same general construction and geometry as described above with respect to the first feedthrough pin 82a, as can the ground pin 84. In some embodiments, immediately adjacent or neighboring ones of the feedthrough pins 82 can bend in opposite directions (e.g., a seen in FIG. 3B, the first and second feedthrough pins 82a, 82b have opposing bend directions such that the second end 112 of the first feedthrough pin 82a is opposite the second end 112 of the second feedthrough pin 82b). In other embodiments, the feedthrough pins 82 can bend in the same direction. Regardless, the feedthrough pins 82 and the ground pin 84 (where provide) are arranged or oriented such that the corresponding trialing regions 116 are substantially co-planar (i.e., within 5% of a truly co-planar relationship). This substantially co-planar relationship can be described or defined, for example, with reference to the trailing region central axis T (FIG. 4A) of the feedthrough pins 82 and the ground pin 84 being substantially co-planar.

Figure 5A:
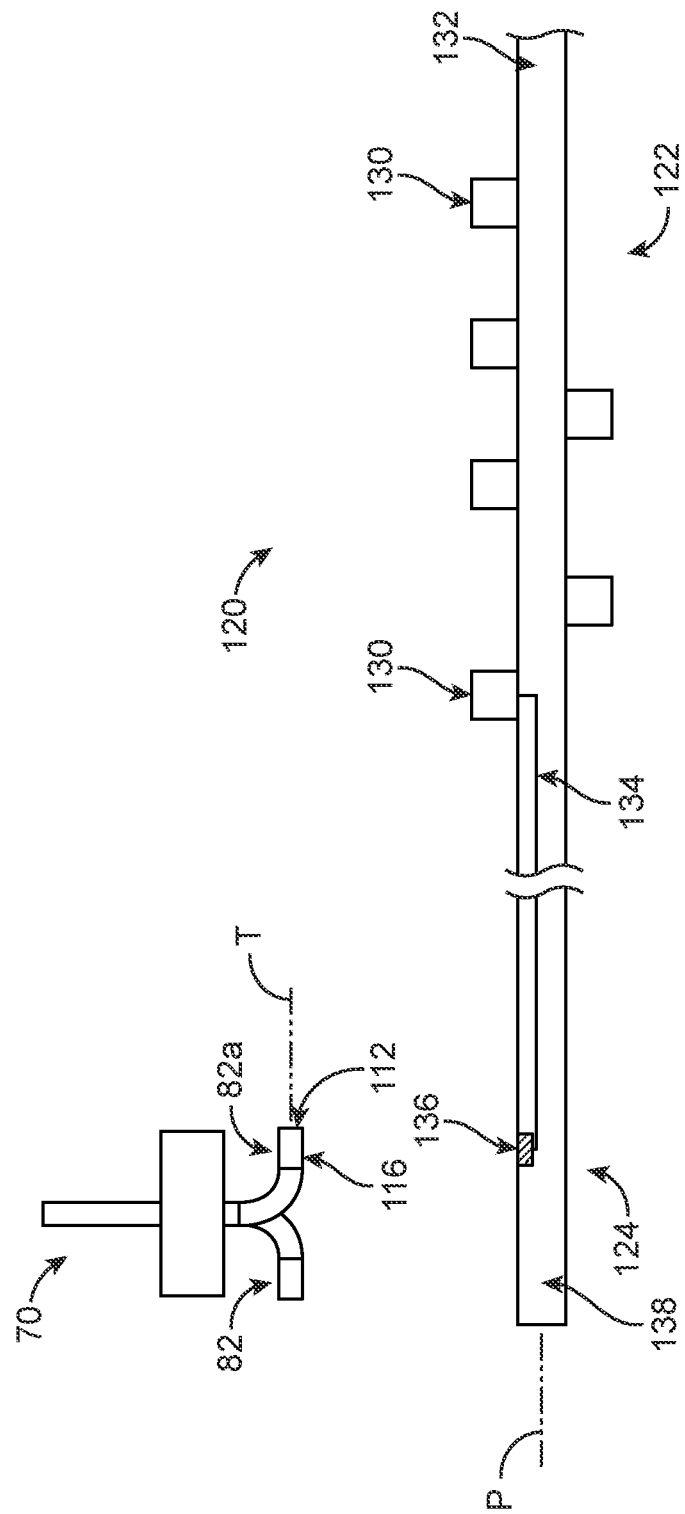

In accordance with some methods of the present disclosure, the interface block 70 (alone or as a sub-assembly of an interface block) facilitates mounting of the feedthrough pins 82 directly to a printed circuit board assembly (PCBA) of the IPG assembly 22 (FIG. 1) as part of the assembly of the IMD 20 (FIG. 1). As a point of reference, FIG. 5A provides a simplified representation of the circuitry 30 (FIG. 1) that can be formed as a PCBA 120. The PCBA 120 can be viewed or described as including or defining a main region 122 and a feedthrough mounting region 124. The main region 122 provides the circuitry 30 appropriate for operation of the IPG assembly 22, and includes various electrical components 130 mounted to or carried by an electrically insulative substrate 132. Various ones of the electrical components 130 are electrically connected to one another by electrically conductive circuitry traces formed in or on the substrate 132. One circuitry trace 134 is shown in FIG. 5A. The circuitry trace 134 is electrically connected to the electrical component 122a and extends to a conductor body 136 of the feedthrough mounting region 124. The conductor body 136 is mounted to or carried by an electrically insulative substrate 138. The substrate 138 of the feedthrough mounting region 124 can be a continuation of the substrate 132 of the main region 122, or can be a separate substrate as described in greater detail below. Though not visible in FIG. 5A, the feedthrough mounting region 124 can include a plurality of the conductor bodies 136, including an individual conductor body for each of the feedthrough pins 82 and the ground pin 84 (FIG. 3A), with each of the individual conductor bodies being electrically connected to a different electrical component 130 by a corresponding circuitry trace.

With the above in mind, some embodiments of the present disclosure include mounting the feedthrough pins 82 and the ground pin 84 (where provided) to the substrate 138 of the feedthrough mounting region 124 via reflow soldering in a manner that establishes electrical connection between the feedthrough pins 82/ground pin 84 and the corresponding conductor body 136. With the non-limiting example of FIG. 5A, the methods of the present disclosure can include placing or laying the feedthrough pins 82 and the ground pin 84 on the substrate 138 such that the corresponding trailing region 116 (FIG. 3A) of each of the feedthrough pins 82 and the ground pin 84 abuts the substrate 138. In some embodiments, an orientation of the each of the feedthrough pins 82 is substantially parallel with the substrate 138 to promote this placement. For example, FIG. 5A identifies a major plane P defined by a shape of the substrate 138. As part of the mounting methodologies of some embodiments of the present disclosure, the interface block 70 is spatially arranged such that the trailing region central axis T of each of the feedthrough pins 82 is generally parallel with the major plane P as reflected by FIG. 5A, and the second end 112 of each of the feedthrough pins 82 is generally aligned with a corresponding conductor body 136 (e.g., in the view of FIG. 5A, the second end 112 of the first feedthrough pin 82a is generally aligned with the illustrated conductor body 136). In some embodiments, the conductor body 136 can be a solder pad or similar construction. Regardless, immediately prior to placement of the feedthrough pins 82 onto the substrate 138, a solder paste or the like is deposited onto one or both of the conductor bodies 136 and/or the trialing region 116 of each of the feedthrough pins 82 (and the ground pin 84).

FIG. 5B illustrates a subsequent step in the mounting process, with the interface block 70 having been directed toward the substrate 138 so as to locate the trailing region 116 of each of the feedthrough pins 82 on the substrate 138. As shown, the second end 112 of the first feedthrough pin 82a is aligned with the conductor body 136. Though not shown, the second end 112 of each of the remaining feedthrough pins 82 is similarly aligned with a corresponding conductor body. The trailing regions 116 collectively sit or lie flat against the substrate 138, with the trailing region central axis T of each of the feedthrough pins 82 (and the ground pin 84 (FIG. 3A)) being substantially parallel with the major plane P of the substrate 138 (i.e., within 5% of a truly parallel relationship).

The assembly of FIG. 5B is then subjected to solder reflowing conditions, for example akin to solder reflow conventionally employed with surface mount technology. For example, the assembly is heated (e.g., in an oven) to a temperature sufficient to cause the solder paste to become molten, followed by cooling. The molten solder cools and hardens, simultaneously establishing a robust, electrical and mechanical connection between each of the feedthrough pins 82 and the corresponding conductor body 136. Unlike conventional feedthrough pin mounting techniques that are complex, expensive, and require additional manufacturing steps and specialized manufacturing equipment, the solder reflow methods of the present disclosure are quickly and inexpensively performed. As a point of reference, in some embodiments the electrical components 130 of the PCBA 120 are similarly mounted to the substrate 132 by solder reflow; with these and related embodiments, the reflow solder mounting of the feedthrough pins 82 and the ground pin 84 to the PCBA 120 can be performed before, simultaneously with, or after solder reflow of the electrical components 130.

Figure 2A:
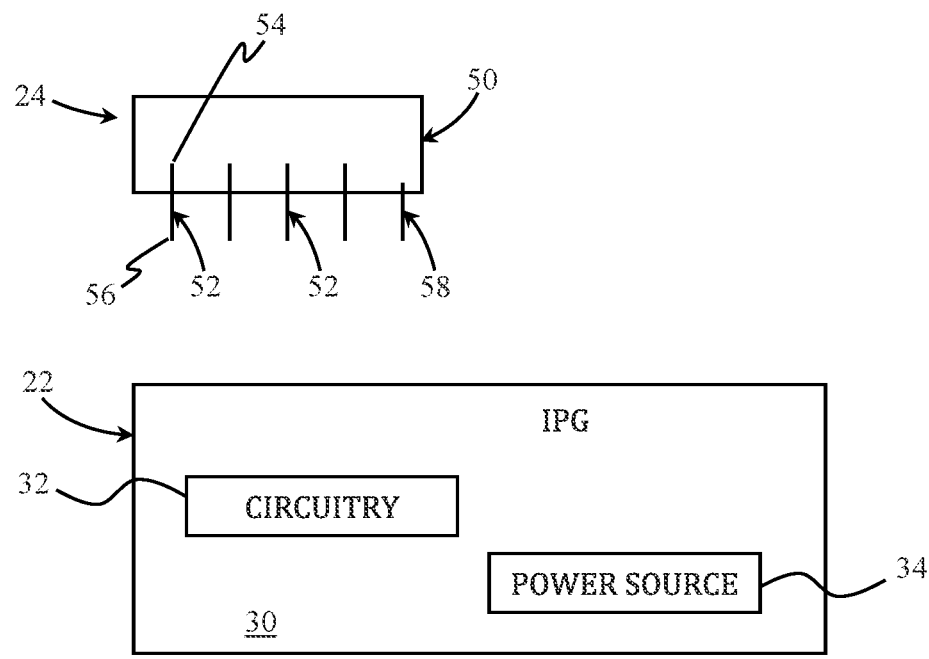
FIG. 2A is a block diagram schematically representing the electronic device of FIG. 1 and in a partially assembled state.
Figure 2B:
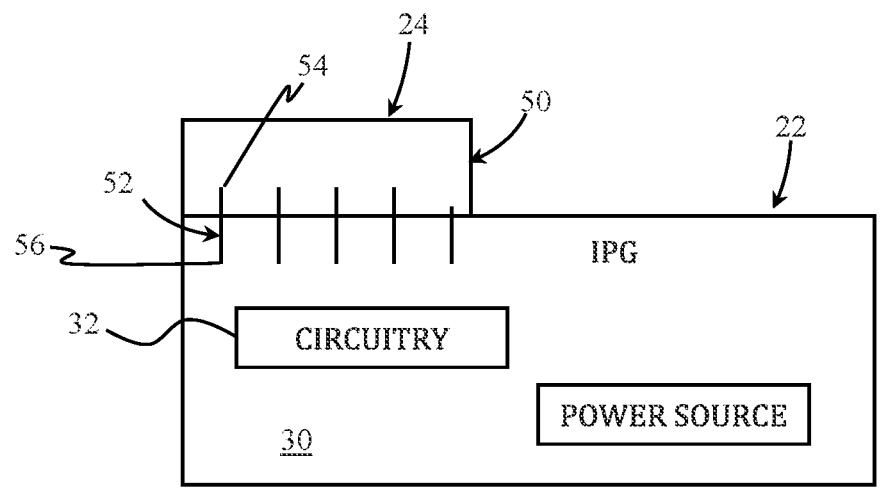
FIG. 2B is a block diagram schematically representing the electronic device of FIG. 2A in an assembled state.
Figure 6:
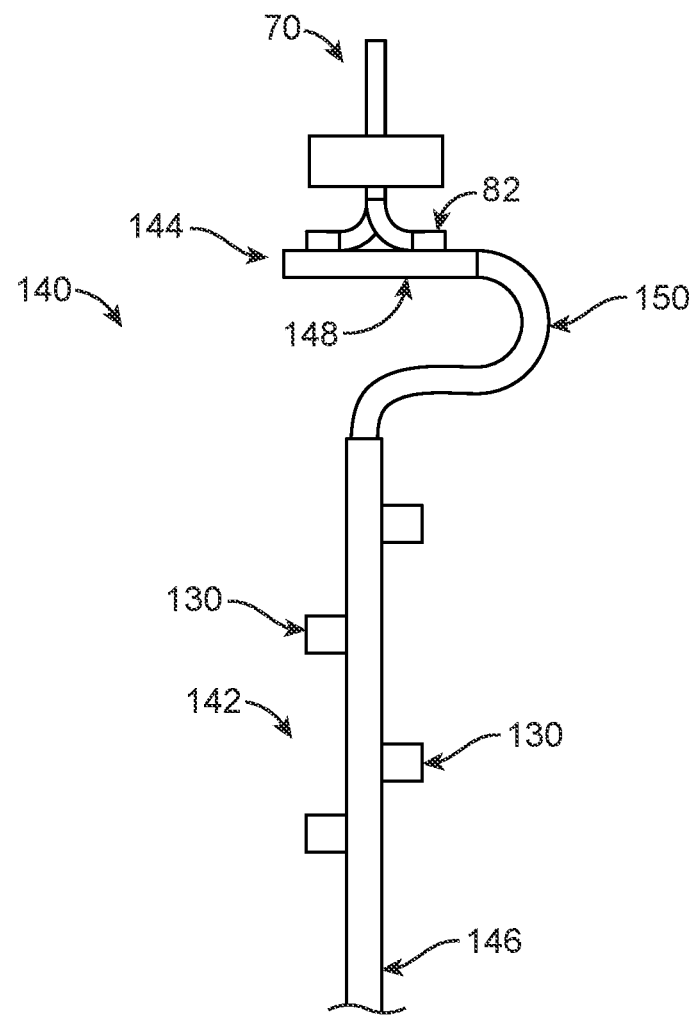
FIG. 6 is a simplified side view of the interface block of FIG. 3A mounted to a printed circuit board assembly for installation within a housing of an electronic device.

With additional reference to FIG. 2A, other methods of the present disclosure can include manufacturing the IPG assembly 22, with these methods implementing the feedthrough pin mounting techniques described above. For example, the feedthrough pins 82/ground pin 84 can be mounted to the PCBA 120 as described above, followed by assembly of the PCBA 120 within the housing 30 and hermetically-sealed attachment of the interface block 70 to the housing 30 (e.g., the arrangement generally reflected in FIG. 4B). In some non-limiting examples, the PCBA 120 can incorporate various substrate features that facilitate compact arrangement between the interface block 70 and the housing 30. For example, FIG. 6 illustrates the interface block 70 mounted to a PCBA 140. The PCBA 140 can be akin to the PCBA 120 (FIG. 5A) described above, and includes a main region 142 and a feedthrough mounting region 144. The electrical components 130 are carried by a substrate 146 of the main region 142, and conductor bodies (not shown) are carried by a substrate 148 of the feedthrough mounting region 144. The main region substrate 146 is connected to the mounting region substrate 148 by an intermediate substrate 150. The intermediate substrate 150 can have a more flexible construction as compared to the main region substrate 146 and the mounting region substrate 148. For example, the main region substrate 146 and the mounting region substrate 148 can be, or can be akin to, rigid PCB boards, whereas the intermediate substrate 150 is, or is akin to, a flex circuit. Alternatively, all three substrates 146-150 can be flexible, or all three substrates 146-150 can be made of a flexible material with additional stiffening element(s) added to the main region 142 and the mounting region 144. Regardless, circuitry traces (not shown) interconnecting the feedthrough pins 82 with corresponding electrical components 130 extend through or along the substrates 146-150. With this construction, the intermediate substrate 150 can be flexed during the manufacturing or assembling process, such that upon final assembly to the housing 30 (not shown), the main region substrate 146 is substantially perpendicular to the mounting region substrate 148 (i.e., within 5 degrees of a truly perpendicular arrangement). Other arrangements are also envisioned, and the present disclosure is not limited to the main region substrate 146 being substantially perpendicular to the mounting region substrate 148 upon final construction of the IPG assembly.

Figure 7A:
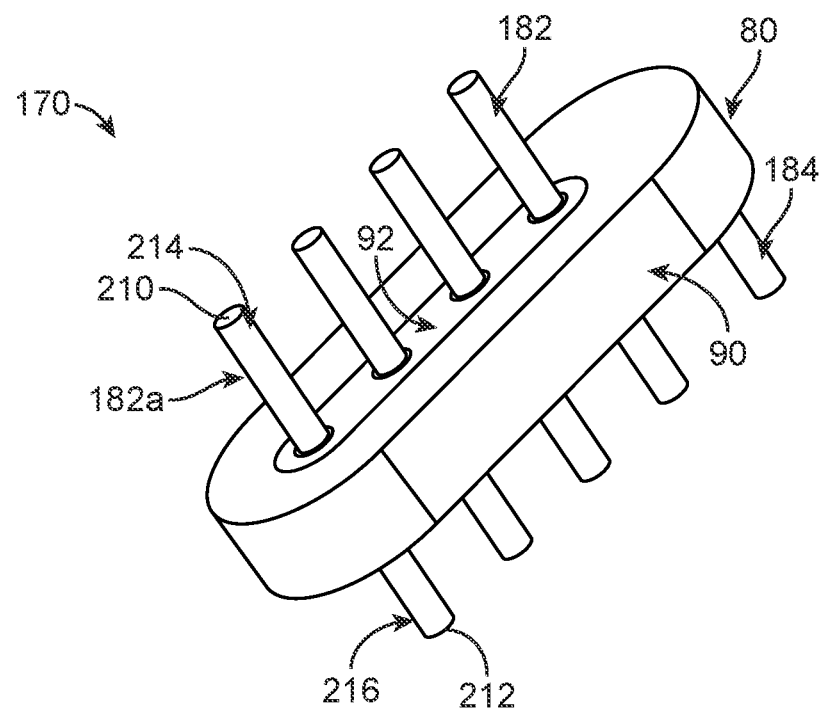
FIG. 7A is a top perspective view of an interface block in accordance with principles of the present disclosure and useful, for example, as the interface block of FIG. 1 or as sub-assembly of the interface block of FIG. 1.
Figure 7B:
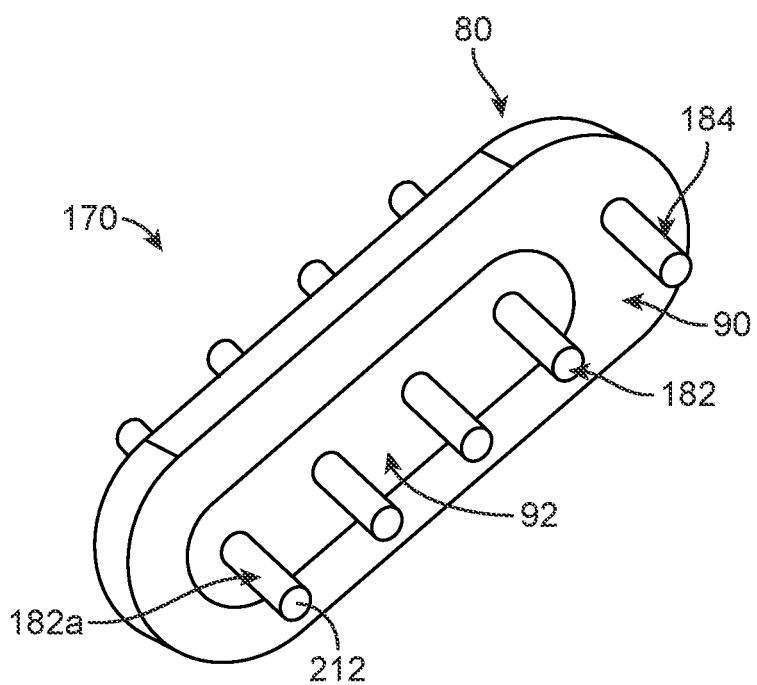
FIG. 7B is a bottom perspective view of the interface block of FIG. 7A.

Another example of an interface block 170 in accordance with principles of the present disclosure and useful as, or as a sub-assembly of, the interface block 24 (FIG. 1) is provided in FIGS. 7A and 7B. The interface block 170 includes the flange assembly 80, one or more feedthrough pins 182, and an optional ground pin 184. The flange assembly 80 maintains the pins 182, 184, and is generally configured for mounting (e.g., hermetically sealed mounting) to the IPG assembly housing 30 (FIG. 1). As described above, the flange assembly 80 can include the flange body 90 and the insulator body 92 (or the insulator body 92 alone in other embodiments). The flange body 90 and the insulator body 92 can have any of the constructions described above.

Figure 7C:
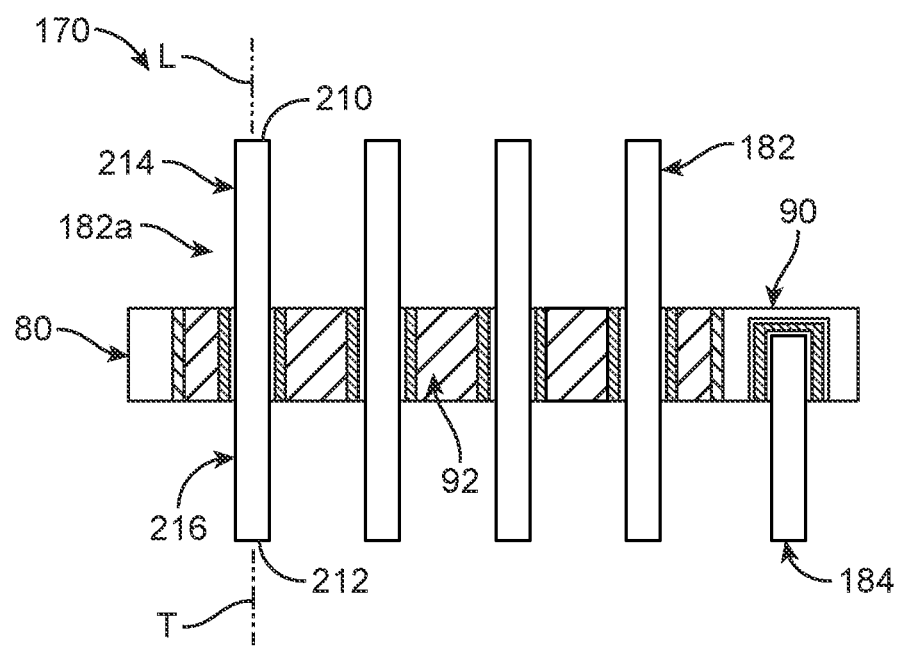
FIG. 7C is a side cross-sectional view of the interface block of FIG. 7A.

With additional reference to FIG. 7C, the insulator body 92 can be secured to the flange body 90 in various manners known in the art and as described above (e.g., a joining material (e.g., brazed gold) can be employed to affix the insulator body 92 to the flange body 90). Regardless, the insulator body 92 defines one or more apertures (not labeled in FIG. 7C, but identified, for example, in FIG. 3C) each sized to receive a corresponding one of the feedthrough pins 182. The feedthrough pin(s) 182 can be affixed to the insulator body 92 via an appropriate joining material (e.g., brazed gold, glass) as described above, as can the ground pin 184.

Each of the feedthrough pins 182 can be viewed as defining or extending between opposing, first and second terminal ends 210, 212 (labeled in FIG. 7A for a first one of the feedthrough pins 182a). As identified in FIG. 7C, a shape of the feedthrough pin 182a defines a leading region 214 extending from and including the first end 210, and an opposing trailing region 216 extending from and including the second end 212. The leading and trailing regions 214, 216, and thus the first and second ends 210, 212 are located or disposed at opposite sides of the flange assembly 80. As described above, an arrangement of the interface block 170 relative to the IPG assembly housing 30 (FIG. 1) upon final assembly is such that the first end 210 is located external the housing 30, whereas the second end 212 is disposed internally within the housing 30. Thus, the feedthrough pin 182a extends between the sealed (e.g., hermetically sealed) interior of the housing 30 and an environment exterior the housing 30.

With the non-limiting example of FIGS. 7A-7C, a shape of each of the feedthrough pins 182 is substantially linear or straight in extension between the first end 210 and the second end 212 (e.g., within 5% of a truly linear or straight arrangement). For example, and as labeled for the first feedthrough pin 182a, the leading region 214 can be viewed as being linear or straight, defining a leading region central axis L; similarly, the trailing region 216 can be viewed as being linear or straight, defining a trailing region central axis T. The leading region central axis L and the trailing region central axis T are substantially co-linear in some embodiments (i.e., within 5% of a truly co-linear arrangement).

Figure 8A:
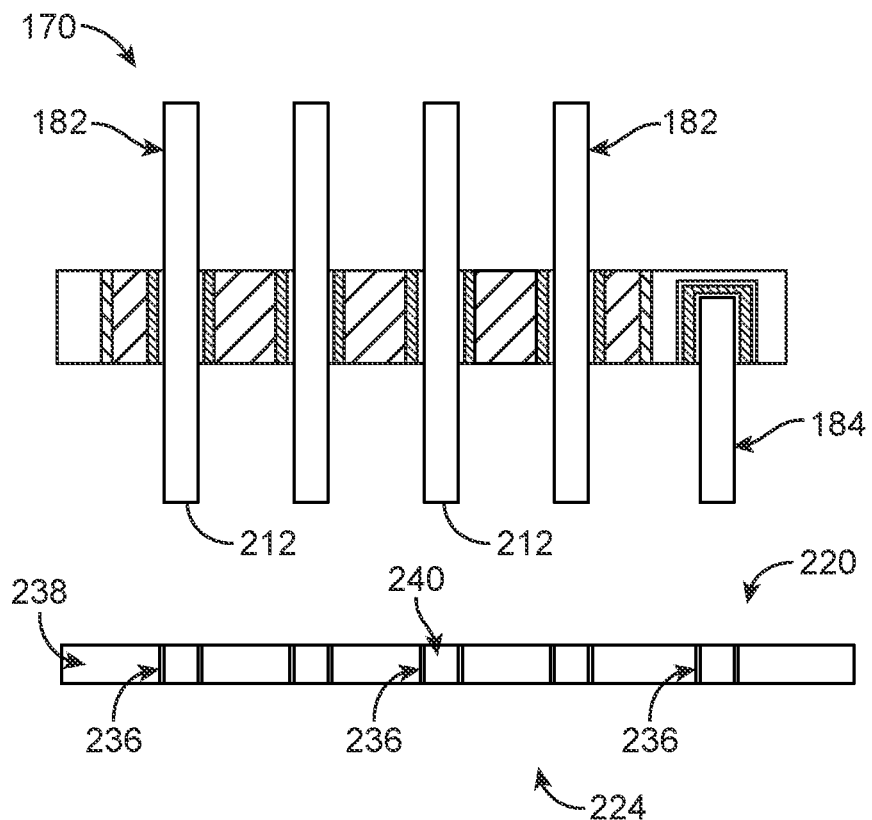
FIGS. 8A and 8B are side views illustrating mounting of feedthrough pins of the interface block of FIG. 7A to a printed circuit board assembly in accordance with methods of the present disclosure.

In accordance with some methods of the present disclosure, the interface block 170 (alone or as a sub-assembly of an interface block) facilitates mounting of the feedthrough pins 182 directly to a printed circuit board assembly (PCBA) of the IPG assembly 22 (FIG. 1) as part of the assembly of the IMD 20 (FIG. 1). As a point of reference, FIG. 8A provides a simplified representation of a portion of a PCBA 220 that can be akin to the PCBA 120 (FIG. 5A) described above. The PCBA 220 can be viewed or described as including or defining a main region (not shown, but akin to the main region 122 (FIG. 5A)) and a feedthrough mounting region 224. The feedthrough mounting region 224 includes a plurality of conductor bodies 236 is mounted to or carried by an electrically insulative substrate 238, for example a conductor body 236 for each of the feedthrough pins 182 and the ground pin 184. In some embodiments, the conductor bodies 236 are each an electrically conductive material plated to or formed within a corresponding through hole 240 in the substrate 238. Thus, in some embodiments, the conductor bodies 236 are, or are akin to, plated vias. Regardless, each of the conductor bodies 236 are electrically connected to a separate circuitry trace (not shown, but akin to the circuitry trace 134 of FIG. 5A) that in turn extends to and is electrically connected to an electrical component (not shown, but akin to the electrical component 130 of FIG. 5A). The substrate 238 of the feedthrough mounting region 224 can be a continuation of the substrate of the main region, or can be a separate substrate.

With the above in mind, some embodiments of the present disclosure include mounting the feedthrough pins 182 and the ground pin 184 (where provided) to the substrate 238 of the feedthrough mounting region 224 via reflow soldering in a manner that establishes electrical connection between the feedthrough pins 182/ground pin 184 and the corresponding conductor body 236. With the non-limiting example of FIG. 8A, the methods of the present disclosure can include aligning the second end 212 of each of the feedthrough pins 182 and the ground pin 184 with a corresponding one of the conductor bodies 236, and then inserting the feedthrough pins 182 and the ground pin 184 into the corresponding conductor body 236. Immediately prior to placement of the feedthrough pins 182 into the corresponding conductor body 236, a solder paste or the like is deposited onto one or both of the conductor bodies 236 and/or the trialing region 216 of each of the feedthrough pins 182 (and the ground pin 184).

Figure 8B:
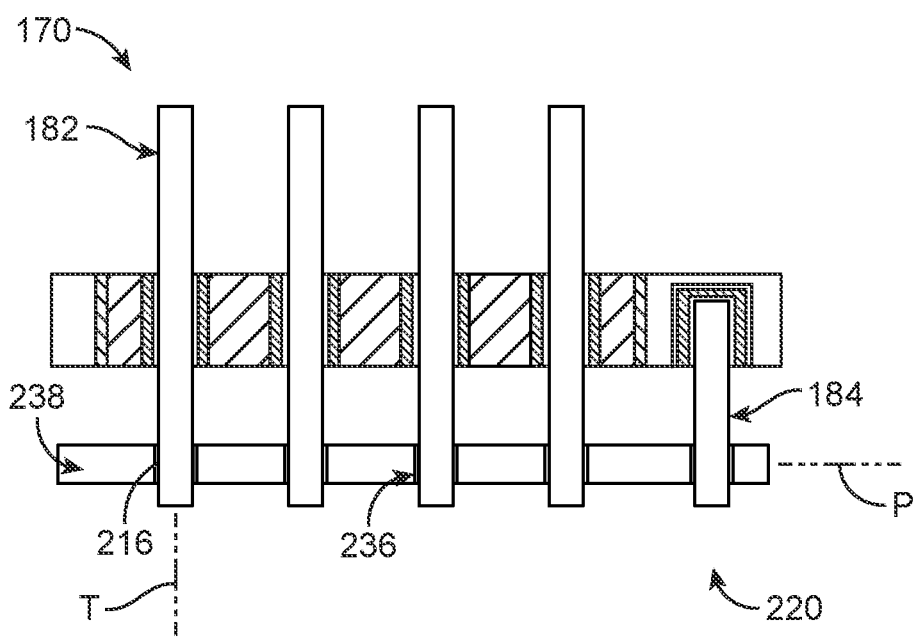

FIG. 8B illustrates a subsequent step in the mounting process, with the interface block 170 having been directed toward the substrate 238 so as to locate the trailing region 216 of each of the feedthrough pins 182 within the corresponding conductor body 236. The trailing regions 216 readily nest within the substrate 238, with the trailing region central axis T of each of the feedthrough pins 182 (and the ground pin 184 being substantially perpendicular to a major plane P of the substrate 238 (i.e., within 5% of a truly perpendicular relationship).

The assembly of FIG. 8B is then subjected to solder reflowing conditions, for example akin to solder reflow conventionally employed with surface mount technology. For example, the assembly is heated (e.g., in an oven) to a temperature sufficient to cause the solder paste to become molten, followed by cooling. The molten solder cools and hardens, simultaneously establishing a robust, electrical and mechanical connection between each of the feedthrough pins 182 and the corresponding conductor body 236. Unlike conventional feedthrough pin mounting techniques that are complex, expensive, and require additional manufacturing steps and specialized manufacturing equipment, the solder reflow methods of the present disclosure are quickly and inexpensively performed. As with other embodiments, the reflow solder mounting of the feedthrough pins 182 and the ground pin 184 to the PCBA 220 can be performed before, simultaneously with, or after solder reflow of the electrical components (not shown, but akin to the electrical components 130 (FIG. 5A) described above. The so-assembled PCBA 220/interface block 170 can be assembled as part of a completed IPG assembly as described above.

Figure 9:
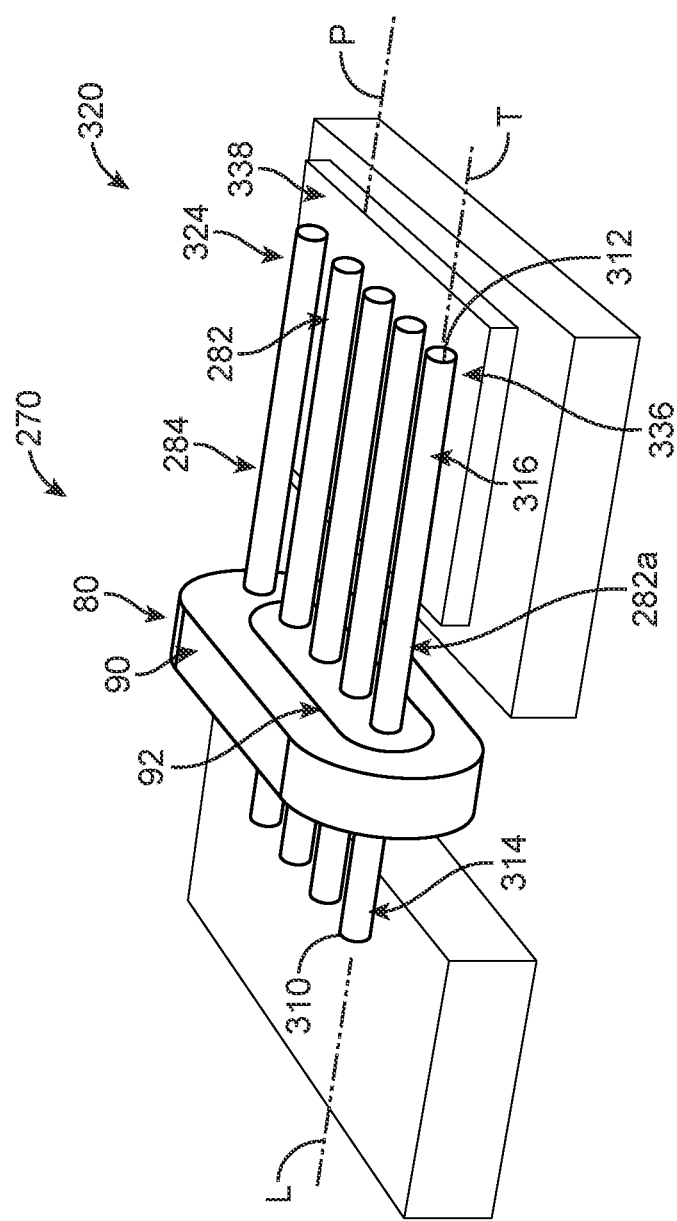
FIG. 9 is a perspective view of an interface block in accordance with principles of the present disclosure and useful, for example, as the interface block of FIG. 1 or as sub-assembly of the interface block of FIG. 1, along with a simplified representation of a printed circuit board assembly.

Another example of an interface block 270 in accordance with principles of the present disclosure and useful as, or as a sub-assembly of, the interface block 24 (FIG. 1) is provided in FIG. 9. The interface block 270 is similar to the interface block 170 (FIG. 7A) and includes the flange assembly 80, one or more feedthrough pins 282, and an optional ground pin 284. The flange assembly 80 maintains the pins 282, 284, and is generally configured for mounting (e.g., hermetically sealed mounting) to the IPG assembly housing 30 (FIG. 1). As described above, the flange assembly 80 can include the flange body 90 and the insulator body 92 (or the insulator body 92 alone in other embodiments). The flange body 90 and the insulator body 92 can have any of the constructions described above. The insulator body 92 can be secured to the flange body 90 in various manners known in the art and as described above (e.g., a joining material (e.g., brazed gold, glass) can be employed to affix the insulator body 92 to the flange body 90). The insulator body 92 defines one or more apertures (not labeled, but identified, for example, in FIG. 3C) each sized to receive a corresponding one of the feedthrough pins 282. The feedthrough pin(s) 282 can be affixed to the insulator body 92 via an appropriate joining material (e.g., brazed gold, glass) as described above, as can the ground pin 284.

Each of the feedthrough pins 282 can be viewed as defining or extending between opposing, first and second terminal ends 310, 312 (labeled in FIG. 9 for a first one of the feedthrough pins 282a). A shape of the feedthrough pin 282a defines a leading region 314 extending from and including the first end 310, and an opposing trailing region 316 extending from and including the second end 312. The leading and trailing regions 314, 316, and thus the first and second ends 310, 312, are located or disposed at opposite sides of the flange assembly 80. As described above, an arrangement of the interface block 270 relative to the IPG assembly housing 30 (FIG. 1) upon final assembly is such that the first end 310 is located external the housing 30, whereas the second end 312 is disposed internally within the housing 30. Thus, the feedthrough pin 282a extends between the sealed (e.g., hermetically sealed) interior of the housing 30 and an environment exterior the housing 30.

With the non-limiting example of FIG. 9, a shape of each of the feedthrough pins 282 is substantially linear or straight in extension between the first end 310 and the second end 312 (e.g., within 5% of a truly linear or straight arrangement). For example, and as labeled for the first feedthrough pin 282a, the leading region 314 can be viewed as being linear or straight, defining a leading region central axis L; similarly, the trailing region 316 can be viewed as being linear or straight, defining a trailing region central axis T. The leading region central axis L and the trailing region central axis T are substantially co-linear in some embodiments (i.e., within 5% of a truly co-linear arrangement).

In accordance with some methods of the present disclosure, the interface block 270 (alone or as a sub-assembly of an interface block) facilitates mounting of the feedthrough pins 282 directly to a printed circuit board assembly (PCBA) of the IPG assembly 22 (FIG. 1) as part of the assembly of the IMD 20 (FIG. 1). As a point of reference, FIG. 9 provides a simplified representation of a portion of a PCBA 320 that can be akin to the PCBA 120 (FIG. 5A) described above. The PCBA 320 can be viewed or described as including or defining a main region (not shown, but akin to the main region 122 (FIG. 5A)) and a feedthrough mounting region 324. The feedthrough mounting region 324 includes a plurality of conductor bodies, one of which is generally referenced at 336, mounted to or carried by an electrically insulative substrate 338, for example one of the conductor bodies 336 for each of the feedthrough pins 282 and the ground pin 284. In some embodiments, each of the conductor bodies 336 are, or are akin to, a solder pad formed on or in the substrate 338. Regardless, each of the conductor bodies 336 are electrically connected to a separate circuitry trace (not shown, but akin to the circuitry trace 134 of FIG. 5A) that in turn extends to and is electrically connected to an electrical component (not shown, but akin to the electrical component 130 of FIG. 5A). The substrate 338 of the feedthrough mounting region 324 can be a continuation of the substrate of the main region, or can be a separate substrate.

With the above in mind, some embodiments of the present disclosure include mounting the feedthrough pins 282 and the ground pin 284 (where provided) to the substrate 338 of the feedthrough mounting region 324 via reflow soldering in a manner that establishes electrical connection between the feedthrough pins 282/ground pin 284 and the corresponding conductor body 336. With the non-limiting example of FIG. 9, the methods of the present disclosure can include laying the trailing region 316 of each of the feedthrough pins 282 and the ground pin 284 on the substrate 338, in general alignment with a corresponding one of the conductor bodies 336. Immediately prior to placement of the feedthrough pins 282 onto the substrate 338, a solder paste or the like is deposited onto one or both of the conductor bodies 336 and/or the trialing region 316 of each of the feedthrough pins 282 (and the ground pin 284).

FIG. 9 illustrates the step in the mounting process in which the interface block 270 has been directed toward the substrate 338 so as to locate the trailing region 316 of each of the feedthrough pins 282 on the substrate 338 in alignment with a corresponding conductor body 336. The trailing regions 316 readily lie flat on the substrate 338, with the trailing region central axis T of each of the feedthrough pins 282 (and the ground pin 284) being substantially parallel with a major plane P (identified generally in FIG. 9) of the substrate 338 (i.e., within 5% of a truly parallel relationship). In some embodiments, the feedthrough pins 282 and the ground pin 284 are co-planar, and can be appropriately supported relative to the substrate 338 during assembly via first and second support blocks 350, 352 (that in turn are placed on a planar support surface). A thickness of the first support block 350 is greater than a thickness of the second support block 352 by a thickness dimension of the substrate 338. With this optional configuration, the substrate 338 is placed on, or supported by, the second support block 353. The leading region 314 of each of the feedthrough pins 282 is placed on, or supported by, the first support block 350, and the trailing region 316 of each of the feedthrough pins 282 and the ground pin 284 naturally lies on the substrate 338.

The assembly of FIG. 9 is then subjected to solder reflowing conditions, for example akin to solder reflow conventionally employed with surface mount technology. For example, the assembly is heated (e.g., in an oven) to a temperature sufficient to cause the solder paste to become molten, followed by cooling. The molten solder cools and hardens, simultaneously establishing a robust, electrical and mechanical connection between each of the feedthrough pins 282 and the corresponding conductor body 336. Unlike conventional feedthrough pin mounting techniques that are complex, expensive, and require additional manufacturing steps and specialized manufacturing equipment, the solder reflow methods of the present disclosure are quickly and inexpensively performed. As with other embodiments, the reflow solder mounting of the feedthrough pins 282 and the ground pin 284 to the PCBA 320 can be performed before, simultaneously with, or after solder reflow of the electrical components (not shown, but akin to the electrical components 130 (FIG. 5A)) described above. The so-assembled PCBA 320/interface block 270 can be assembled as part of a completed IPG assembly as described above.

Figure 10A:
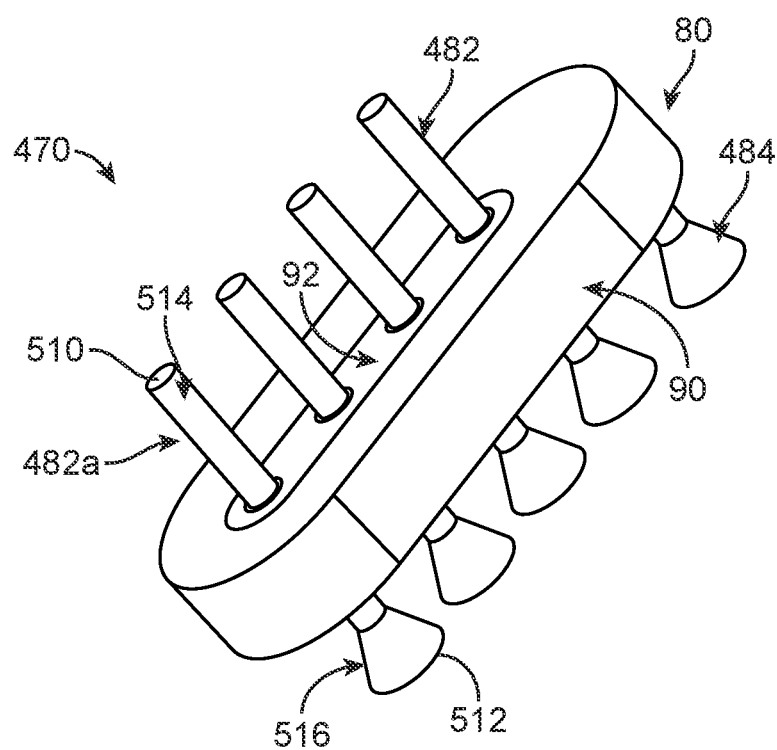
FIG. 10A is a top perspective view of an interface block in accordance with principles of the present disclosure and useful, for example, as the interface block of FIG. 1 or as sub-assembly of the interface block of FIG. 1.
Figure 10B:
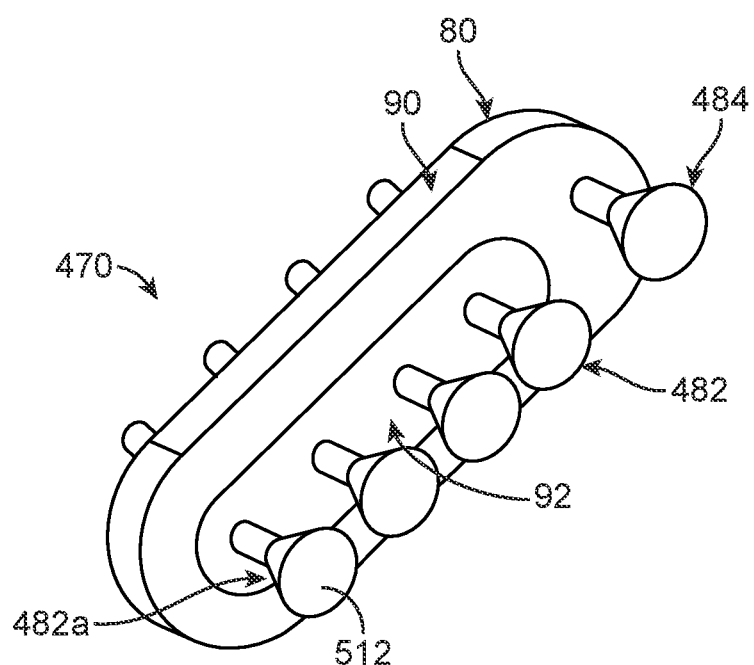
FIG. 10B is a bottom perspective view of the interface block of FIG. 10A.

Another example of an interface block 470 in accordance with principles of the present disclosure and useful as, or as a sub-assembly of, the interface block 24 (FIG. 1) is provided in FIGS. 10A and 10B. The interface block 470 includes the flange assembly 80, one or more feedthrough pins 482, and an optional ground pin 484. The flange assembly 80 maintains the pins 482, 484, and is generally configured for mounting (e.g., hermetically sealed mounting) to the IPG assembly housing 30 (FIG. 1). As described above, the flange assembly 80 can include the flange body 90 and the insulator body 92 (or the insulator body 92 alone in other embodiments). The flange body 90 and the insulator body 92 can have any of the constructions described above.

Figure 10C:
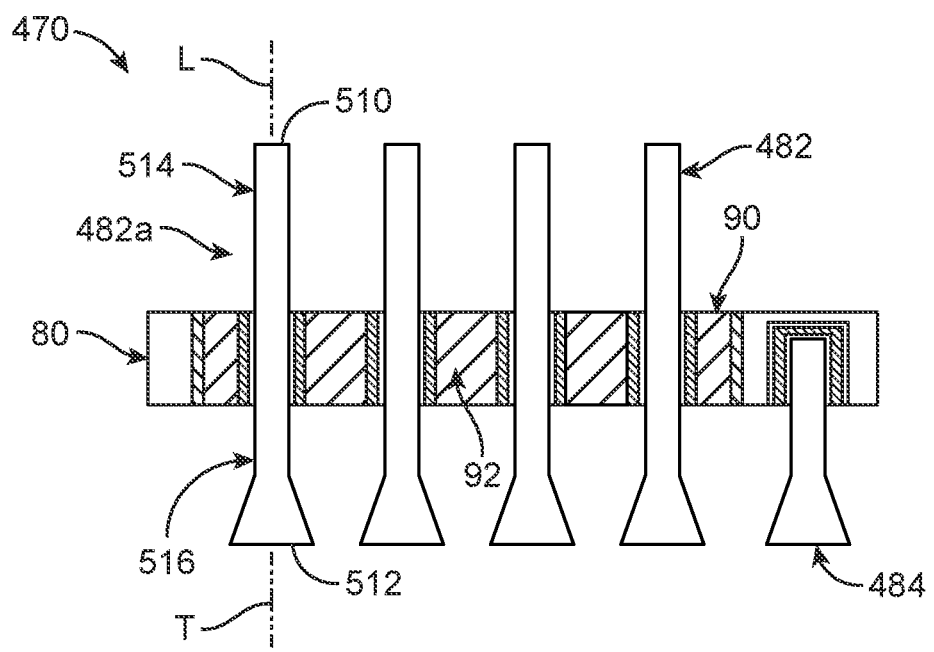
FIG. 10C is a side cross-sectional view of the interface block of FIG. 10A.

With additional reference to FIG. 10C, the insulator body 92 can be secured to the flange body 90 in various manners known in the art and as described above (e.g., a joining material (e.g., brazed gold, glass) can be employed to affix the insulator body 92 to the flange body 90). Regardless, the insulator body 92 defines one or more apertures (not labeled in FIG. 10C, but identified, for example, in FIG. 3C) each sized to receive a corresponding one of the feedthrough pins 482. The feedthrough pin(s) 482 can be affixed to the insulator body 92 via an appropriate joining material (e.g., brazed gold, glass) as described above, as can the ground pin 484.

Each of the feedthrough pins 482 can be viewed as defining or extending between opposing, first and second terminal ends 510, 512 (labeled in FIG. 10A for a first one of the feedthrough pins 482a). As identified in FIG. 10C, a shape of the feedthrough pin 482a defines a leading region 514 extending from and including the first end 510, and an opposing trailing region 516 extending from and including the second end 512. The leading and trailing regions 514, 516, and thus the first and second ends 510, 512 are located or disposed at opposite sides of the flange assembly 80. As described above, an arrangement of the interface block 470 relative to the IPG assembly housing 30 (FIG. 1) upon final assembly is such that the first end 510 is located external the housing 30, whereas the second end 512 is disposed internally within the housing 30. Thus, the feedthrough pin 482a extends between the sealed (e.g., hermetically sealed) interior of the housing 30 and an environment exterior the housing 30.

With the non-limiting example of FIGS. 10A-10C, a shape of each of the feedthrough pins 482 is such that a centerline thereof is substantially linear or straight in extension between the first end 510 and the second end 512 (e.g., within 5% of a truly linear or straight arrangement). For example, and as labeled for the first feedthrough pin 482a, the leading region 514 can be viewed as defining a leading region central axis L that is linear or straight; similarly, the trailing region 516 can be viewed as defining a trailing region central axis T that is linear or straight. The leading region central axis L and the trailing region central axis T are substantially co-linear in some embodiments (i.e., within 5% of a truly co-linear arrangement). An exterior shape or geometry of the feedthrough pins 482 along the corresponding leading region 514 can be substantially uniform or constant. For example, an outer diameter of each of the feedthrough pins 482 along the corresponding leading region 514 in extension from the first end 510 can be substantially constant or uniform (i.e., within 5% of a truly uniform diameter). An exterior shape or geometry of each of the feedthrough pins 482 along the corresponding trailing region 516 can be non-constant or non-uniform. For example, an outer diameter of each of the feedthrough pins 482 can taper in extension from the corresponding second end 512. In some embodiments, the outer diameter of the second end 512 is greater than the outer diameter of the first end 510. The outer diameter of each of the feedthrough pins 482 (as well as the ground pin 484) can taper from the corresponding second end 512. Stated otherwise, the trailing region 516 of each of the feedthrough pins 482 (as well as the ground pin 484) can flare or define an expanding diameter in extension to the second end 512. The trailing region 516 can be an integrally formed segment of the feedthrough pin 482, or can be an electrically conductive body formed on or attached to a pin otherwise having a uniform diameter.

Figure 11A:
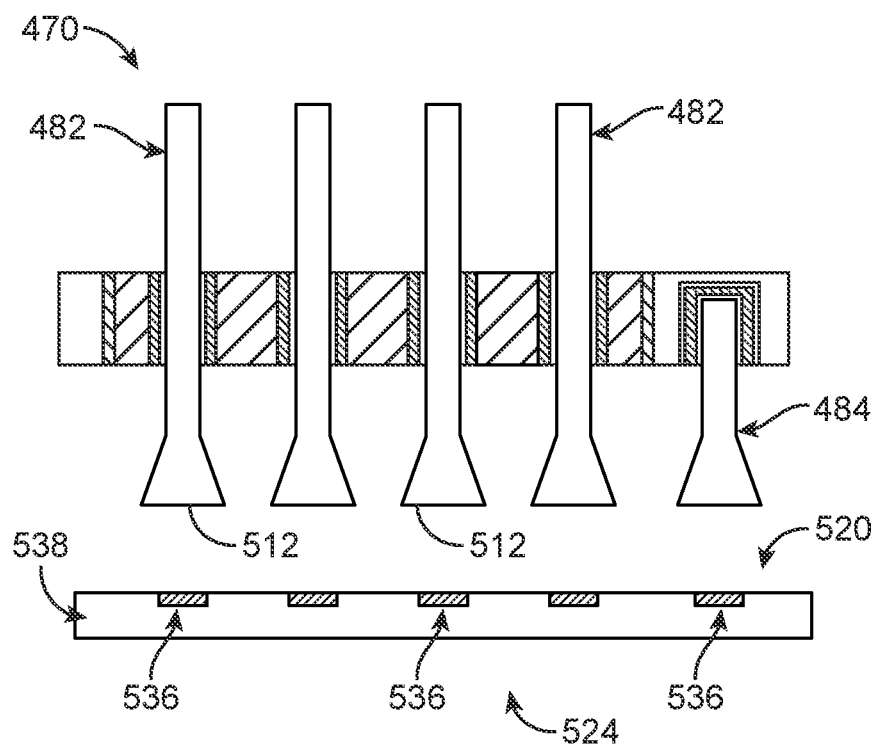
FIGS. 11A and 11B are side views illustrating mounting of feedthrough pins of the interface block of FIG. 10A to a printed circuit board assembly in accordance with methods of the present disclosure.

In accordance with some methods of the present disclosure, the interface block 470 (alone or as a sub-assembly of an interface block) facilitates mounting of the feedthrough pins 482 directly to a printed circuit board assembly (PCBA) of the IPG assembly 22 (FIG. 1) as part of the assembly of the IMD 20 (FIG. 1). As a point of reference, FIG. 11A provides a simplified representation of a portion of a PCBA 520 that can be akin to the PCBA 120 (FIG. 5A) described above. The PCBA 520 can be viewed or described as including or defining a main region (not shown, but akin to the main region 122 (FIG. 5A)) and a feedthrough mounting region 524. The feedthrough mounting region 524 includes a plurality of conductor bodies 536 mounted to or carried by an electrically insulative substrate 538, for example a conductor body 536 for each of the feedthrough pins 482 and the ground pin 484. In some embodiments, each of the conductor bodies 536 are, or are akin to, a solder pad formed on or in the substrate 538. Regardless, each of the conductor bodies 536 are electrically connected to a separate circuitry trace (not shown, but akin to the circuitry trace 134 of FIG. 5A) that in turn extends to and is electrically connected to an electrical component (not shown, but akin to the electrical component 130 of FIG. 5A). The substrate 538 of the feedthrough mounting region 524 can be a continuation of the substrate of the main region, or can be a separate substrate.

With the above in mind, some embodiments of the present disclosure include mounting the feedthrough pins 482 and the ground pin 484 (where provided) to the substrate 538 of the feedthrough mounting region 524 via reflow soldering in a manner that establishes electrical connection between the feedthrough pins 482/ground pin 484 and the corresponding conductor body 536. With the non-limiting example of FIG. 11A, the methods of the present disclosure can include aligning the second end 512 of each of the feedthrough pins 482 and the ground pin 484 with a corresponding one of the conductor bodies 536, and then placing the second end 512 of each of the feedthrough pins 482 and the ground pin 484 onto the corresponding conductor body 536 (and thus on or against the substrate 538). Immediately prior to placement of the feedthrough pins 482 into the corresponding conductor body 536, a solder paste or the like is deposited onto one or both of the conductor bodies 536 and/or the trialing region 416 (and in particular the second end 512) of each of the feedthrough pins 482 (and the ground pin 484).

Figure 11B:
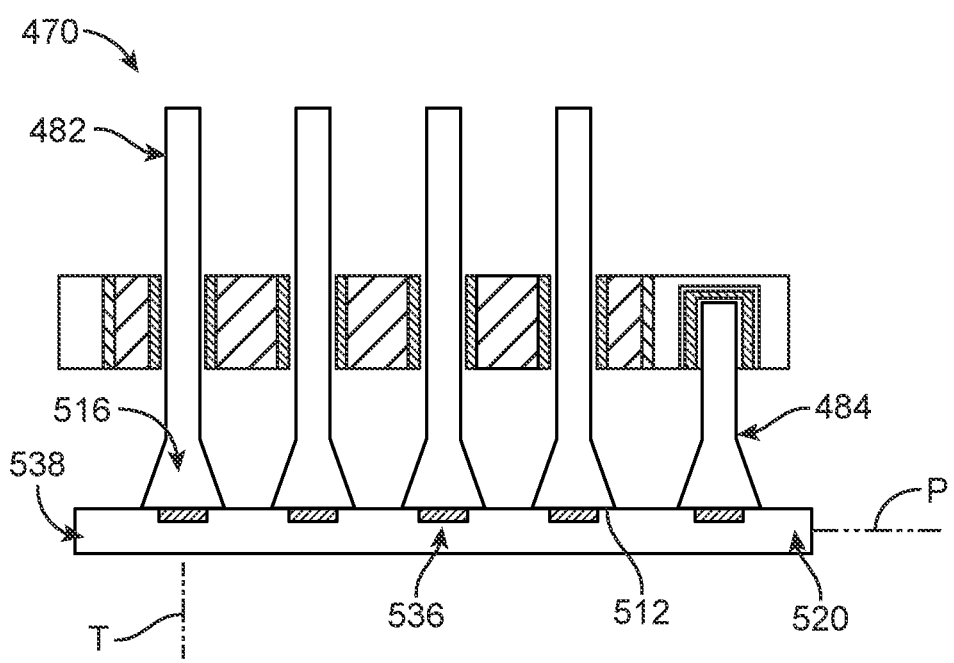

FIG. 11B illustrates a subsequent step in the mounting process, with the interface block 470 having been directed toward the substrate 538 so as to locate the second end 512 of each of the feedthrough pins 482 on the corresponding conductor body 536. The second ends 512 collectively rest against or abut the substrate 538, with the trailing region central axis T of each of the feedthrough pins 482 (and the ground pin 484) being substantially perpendicular to a major plane P of the substrate 538 (i.e., within 5% of a truly perpendicular relationship).

The assembly of FIG. 11B is then subjected to solder reflowing conditions, for example akin to solder reflow conventionally employed with surface mount technology. For example, the assembly is heated (e.g., in an oven) to a temperature sufficient to cause the solder paste to become molten, followed by cooling. The molten solder cools and hardens, simultaneously establishing a robust, electrical and mechanical connection between each of the feedthrough pins 482 and the corresponding conductor body 536. Unlike conventional feedthrough pin mounting techniques that are complex, expensive, and require additional manufacturing steps and specialized manufacturing equipment, the solder reflow methods of the present disclosure are quickly and inexpensively performed. As with other embodiments, the reflow solder mounting of the feedthrough pins 482 and the ground pin 484 to the PCBA 520 can be performed before, simultaneously with, or after solder reflow of the electrical components (not shown, but akin to the electrical components 130 (FIG. 5A)) described above. The so-assembled PCBA 520/interface block 470 can be assembled as part of a completed IPG assembly as described above.

Figure 12A:
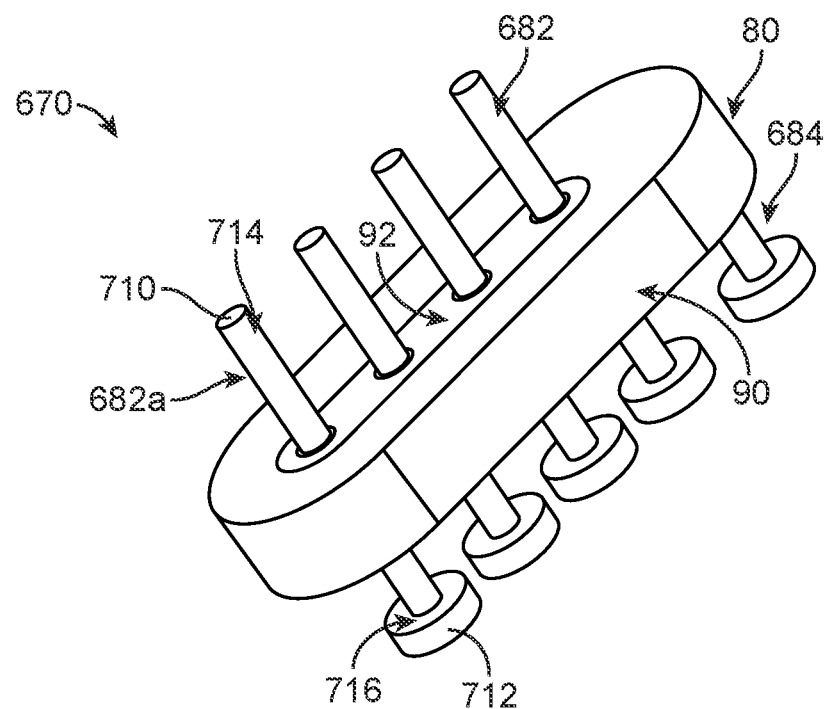
FIG. 12A is a top perspective view of an interface block in accordance with principles of the present disclosure and useful, for example, as the interface block of FIG. 1 or as sub-assembly of the interface block of FIG. 1.
Figure 12B:
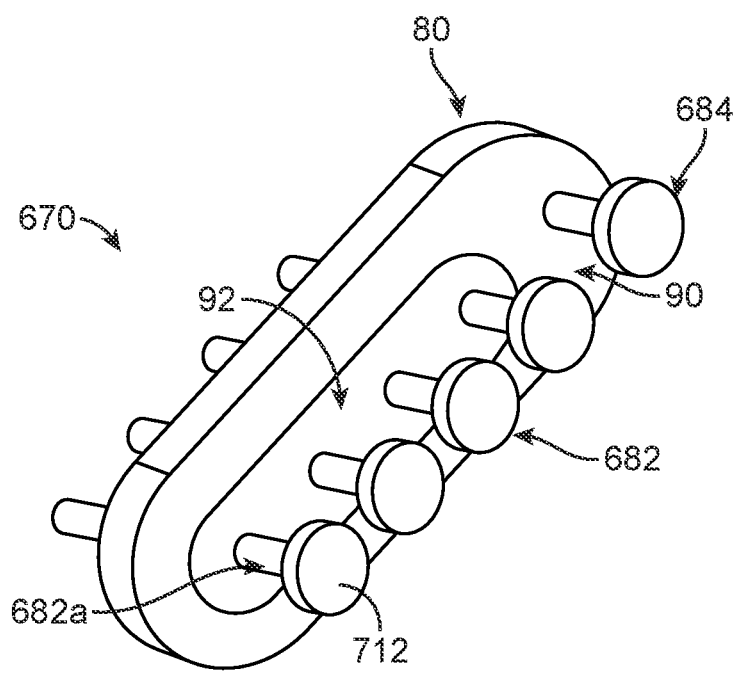
FIG. 12B is a bottom perspective view of the interface block of FIG. 12A.

Another example of an interface block 670 in accordance with principles of the present disclosure and useful as, or as a sub-assembly of, the interface block 24 (FIG. 1) is provided in FIGS. 12A and 12B. The interface block 670 includes the flange assembly 80, one or more feedthrough pins 682, and an optional ground pin 684. The flange assembly 80 maintains the pins 682, 684, and is generally configured for mounting (e.g., hermetically sealed mounting) to the IPG assembly housing 30 (FIG. 1). As described above, the flange assembly 80 can include the flange body 90 and the insulator body 92 (or the insulator body 92 alone in other embodiments). The flange body 90 and the insulator body 92 can have any of the constructions described above.

Figure 12C:
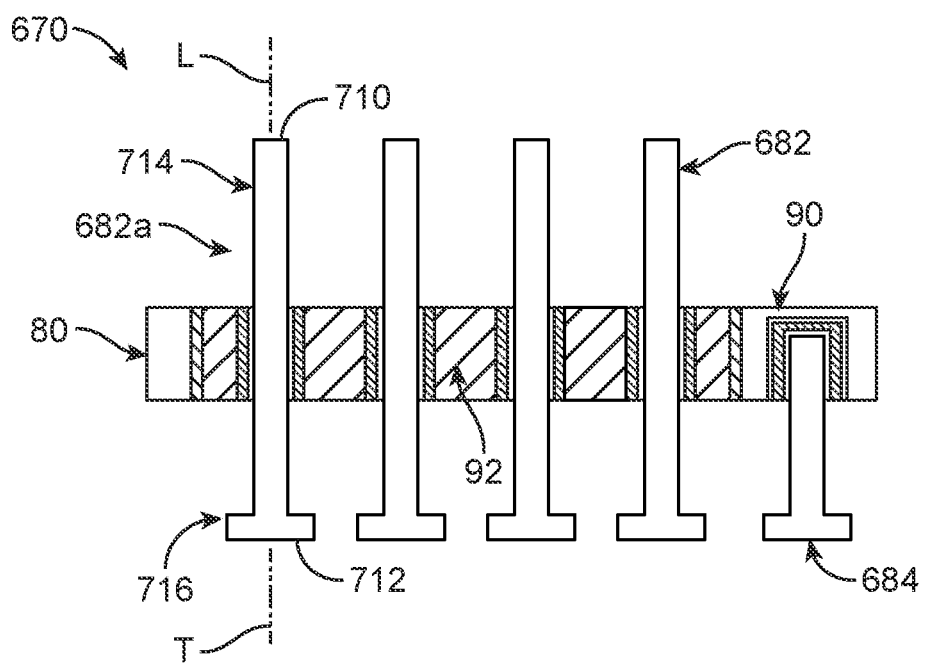
FIG. 12C is a side cross-sectional view of the interface block of FIG. 12A.

With additional reference to FIG. 12C, the insulator body 92 can be secured to the flange body 90 in various manners known in the art and as described above (e.g., a joining material (e.g., brazed gold, glass) can be employed to affix the insulator body 92 to the flange body 90). Regardless, the insulator body 92 defines one or more apertures (not labeled in FIG. 12C, but identified, for example, in FIG. 3C) each sized to receive a corresponding one of the feedthrough pins 682. The feedthrough pin(s) 682 can be affixed to the insulator body 92 via an appropriate joining material (e.g., brazed gold, glass) as described above, as can the ground pin 684.

Each of the feedthrough pins 682 can be viewed as defining or extending between opposing, first and second terminal ends 710, 712 (labeled in FIG. 12A for a first one of the feedthrough pins 682a). As identified in FIG. 12C, a shape of the feedthrough pin 682a defines a leading region 714 extending from and including the first end 710, and an opposing trailing region 716 extending from and including the second end 712. The leading and trailing regions 714, 716, and thus the first and second ends 710, 712 are located or disposed at opposite sides of the flange assembly 80. As described above, an arrangement of the interface block 670 relative to the IPG assembly housing 30 (FIG. 1) upon final assembly is such that the first end 710 is located external the housing 30, whereas the second end 712 is disposed internally within the housing 30. Thus, the feedthrough pin 682a extends between the sealed (e.g., hermetically sealed) interior of the housing 30 and an environment exterior the housing 30.

Figure 12D:
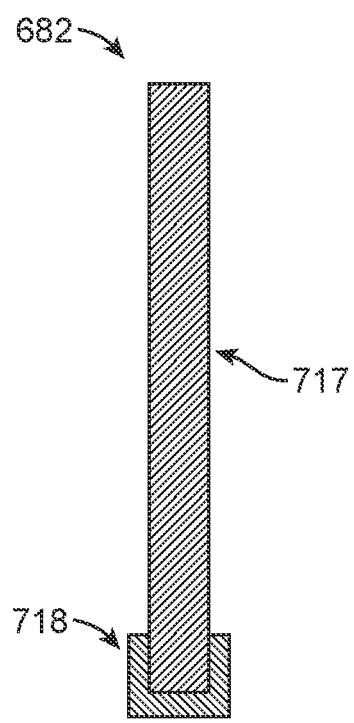
FIG. 12D is a simplified cross-sectional view of a feedthrough pin useful with the interface block of FIG. 12A.

With the non-limiting example of FIGS. 12A-12C, a shape of each of the feedthrough pins 682 is such that a centerline thereof is substantially linear or straight in extension between the first end 710 and the second end 712 (e.g., within 5% of a truly linear or straight arrangement). For example, and as labeled for the first feedthrough pin 682a, the leading region 714 can be viewed as defining a leading region central axis L that is linear or straight; similarly, the trailing region 716 can be viewed as defining a trailing region central axis T that is linear or straight. The leading region central axis L and the trailing region central axis T are substantially co-linear in some embodiments (i.e., within 5% of a truly co-linear arrangement). An exterior shape or geometry of the feedthrough pins 682 along the corresponding leading region 714 can be substantially uniform or constant. For example, an outer diameter of each of the feedthrough pins 682 along the corresponding leading region 714 in extension from the first end 710 can be substantially constant or uniform (i.e., within 5% of a truly uniform diameter). An exterior shape or geometry of each of the feedthrough pins 682 along the corresponding trailing region 716 can be non-constant or non-uniform. For example, each of the feedthrough pins 682 can have an enlarged outer diameter at the second end 712 as compared to a diameter of a remainder of the trailing region 716. In some embodiments, the outer diameter of the second end 712 is greater than the outer diameter of the first end 710. The trailing region 716 can be an integrally formed segment of the feedthrough pin 682, or can be an electrically conductive body formed on or attached to a pin otherwise having a uniform diameter. This optional secondary body attached to the pin can be made of a material differing from a material of the pin and that is selected to enhance strength and reliability of the solder joint. For example, and as shown in FIG. 12D, the feedthrough pin 682 can include a pin body 717 and a secondary body 718. The pin body 717 can have a substantially uniform outer diameter (the ground pin 84 (FIG. 12A) can have a similar construction). In some embodiments, the secondary body 718 can have a cup-like or ring-like shape and is joined to an outer surface of the pin body 717. In other embodiments, the secondary body 718 can be akin to a solid disc joined to an end of the pin body 717. The secondary body 718 (e.g., a metal body) can be joined to the pin body 717 in various manners, for example weld (laser, resistance, etc.), solder reflow, crimp, swaged, etc. With embodiments in which the secondary body 718 is joined to the pin body 717 by solder reflow, a solder differing from that utilized with subsequent solder reflow to the printed circuit board assembly (described below) can be employed, for example a solder having a melting point that differs from that of subsequent solder reflow to the printed circuit board assembly. Thus, some methods of the present disclosure include joining a secondary body a pin body by laser welding, resistance welding, solder reflow, crimping, swaging, etc.

Figure 13A:
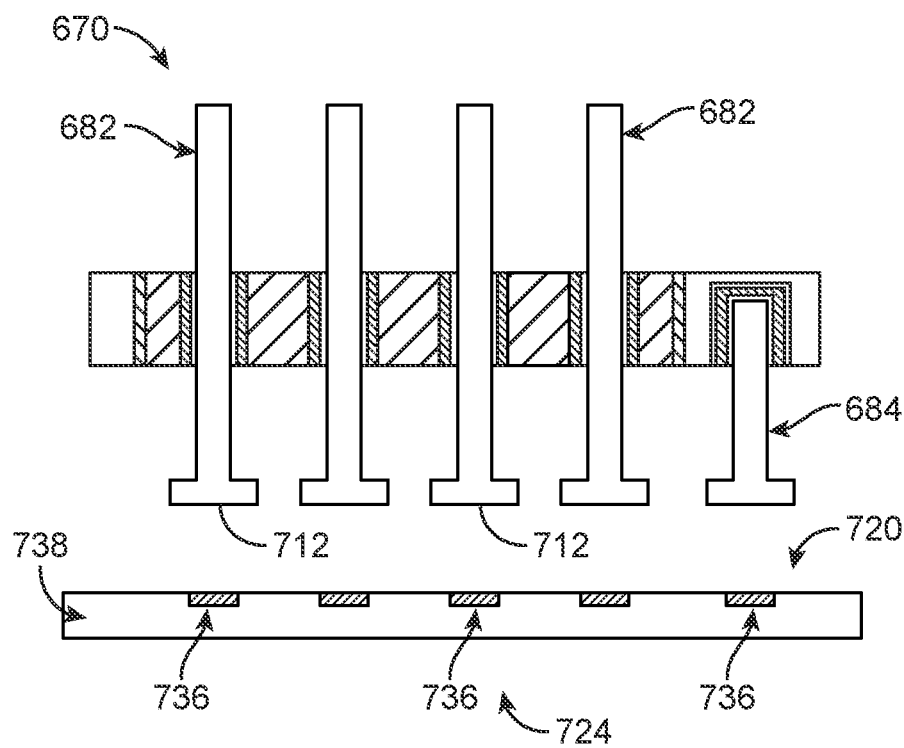
FIGS. 13A and 13B are side views illustrating mounting of feedthrough pins of the interface block of FIG. 12A to a printed circuit board assembly in accordance with methods of the present disclosure.

In accordance with some methods of the present disclosure, the interface block 670 (alone or as a sub-assembly of an interface block) facilitates mounting of the feedthrough pins 682 directly to a printed circuit board assembly (PCBA) of the IPG assembly 22 (FIG. 1) as part of the assembly of the IMD 20 (FIG. 1). As a point of reference, FIG. 13A provides a simplified representation of a portion of a PCBA 720 that can be akin to the PCBA 120 (FIG. 5A) described above. The PCBA 720 can be viewed or described as including or defining a main region (not shown, but akin to the main region 122 (FIG. 5A)) and a feedthrough mounting region 724. The feedthrough mounting region 724 includes a plurality of conductor bodies 736 mounted to or carried by an electrically insulative substrate 738, for example a conductor body 736 for each of the feedthrough pins 682 and the ground pin 684. In some embodiments, each of the conductor bodies 736 are, or are akin to, a solder pad formed on or in the substrate 738. Regardless, each of the conductor bodies 736 are electrically connected to a separate circuitry trace (not shown, but akin to the circuitry trace 134 of FIG. 5A) that in turn extends to and is electrically connected to an electrical component (not shown, but akin to the electrical component 130 of FIG. 5A). The substrate 738 of the feedthrough mounting region 724 can be a continuation of the substrate of the main region, or can be a separate substrate.

With the above in mind, some embodiments of the present disclosure include mounting the feedthrough pins 682 and the ground pin 684 (where provided) to the substrate 738 of the feedthrough mounting region 724 via reflow soldering in a manner that establishes electrical connection between the feedthrough pins 682/ground pin 684 and the corresponding conductor body 736. With the non-limiting example of FIG. 13A, the methods of the present disclosure can include aligning the second end 712 of each of the feedthrough pins 682 and the ground pin 684 with a corresponding one of the conductor bodies 736, and then placing the second end 712 of each of the feedthrough pins 682 and the ground pin 684 onto the corresponding conductor body 736 (and thus on or against the substrate 738). Immediately prior to placement of the feedthrough pins 682 into the corresponding conductor body 736, a solder paste or the like is deposited onto one or both of the conductor bodies 736 and/or the trialing region 616 (and in particular the second end 712) of each of the feedthrough pins 682 (and the ground pin 684).

Figure 13B:
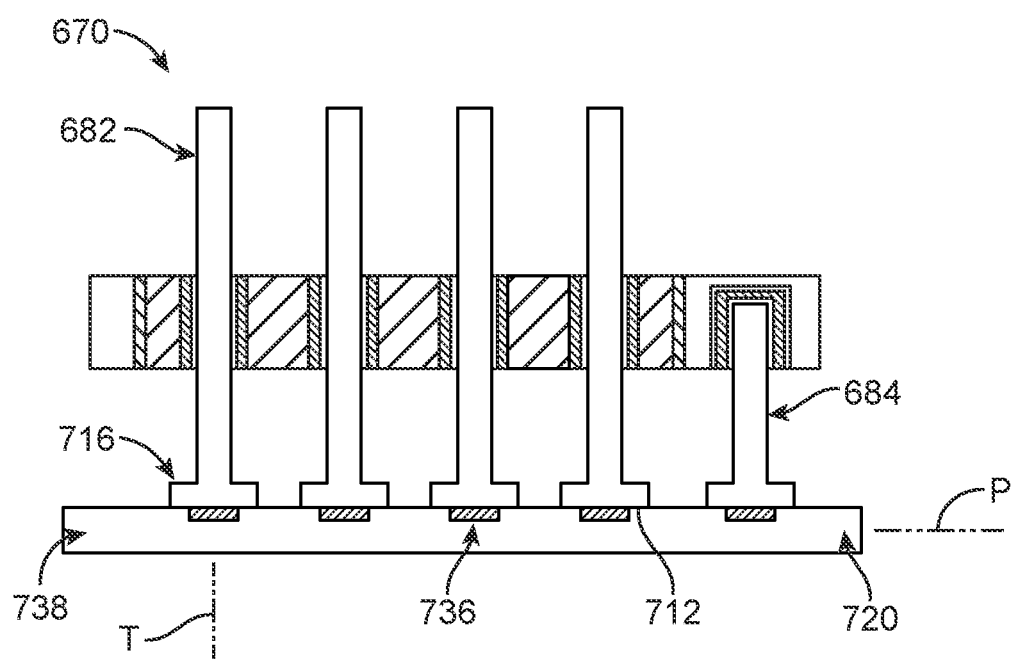

FIG. 13B illustrates a subsequent step in the mounting process, with the interface block 670 having been directed toward the substrate 738 so as to locate the second end 712 of each of the feedthrough pins 682 on the corresponding conductor body 736. The second ends 712 collectively rest against or abut the substrate 738, with the trailing region central axis T of each of the feedthrough pins 682 (and the ground pin 684) being substantially perpendicular to a major plane P of the substrate 738 (i.e., within 5% of a truly perpendicular relationship).

The assembly of FIG. 13B is then subjected to solder reflowing conditions, for example akin to solder reflow conventionally employed with surface mount technology. For example, the assembly is heated (e.g., in an oven) to a temperature sufficient to cause the solder paste to become molten, followed by cooling. The molten solder cools and hardens, simultaneously establishing a robust, electrical and mechanical connection between each of the feedthrough pins 682 and the corresponding conductor body 736. Unlike conventional feedthrough pin mounting techniques that are complex, expensive, and require additional manufacturing steps and specialized manufacturing equipment, the solder reflow methods of the present disclosure are quickly and inexpensively performed. As with other embodiments, the reflow solder mounting of the feedthrough pins 682 and the ground pin 684 to the PCBA 720 can be performed before, simultaneously with, or after solder reflow of the electrical components (not shown, but akin to the electrical components 130 (FIG. 5A)) described above. The so-assembled PCBA 720/interface block 670 can be assembled as part of a completed IPG assembly as described above.

With any of the embodiments and methods of FIGS. 1-13B, formation the corresponding feedthrough pin(s) and/or ground pin in accordance with non-limiting examples of the present disclosure can include surface plating or surface coating (e.g., gold plating) to enhance strength and reliability of the subsequently-formed solder joint. With any of the embodiments and methods of FIGS. 1-13B, the feedthrough pins can be arranged in any geometry and any number of the feedthrough pins can be provided. Thus, while several of the views illustrate the provision of four feedthrough pins and a ground pin arranged in a linear fashion, the present disclosure is in no way limited. With any of the embodiments, a greater or lesser number of feedthrough pins can be provided and/or the feedthrough pins can be arranged in an array-like fashion (e.g., 2×4, 2×6, etc.) and/or have offset or staggered rows.

Returning to FIGS. 1-2B, the interface blocks 24 of the present disclosure (and corresponding methods of solder reflow bonding of the feedthrough pin(s) 52 and the ground pin 54 (where provided) to internal electronics of a hermetically sealed device can be useful as part of the IMD 20 that further includes the stimulation lead 40. In some embodiments, the stimulation lead 40 includes a lead body 62 with a distally located stimulation electrode 64. At an opposite end of the lead body 62, the stimulation lead 40 includes the proximally located plug-in connector 60 which is configured to be removably connectable to the interface block 24 (e.g., the interface block 24 can optionally include or provide a stimulation port sized and shaped to receive the plug-in connector 60 as is known in the art).

In general terms, the stimulation electrode 64 can optionally be a cuff electrode, and can include some non-conductive structures biased to (or otherwise configurable to) releasable secure the stimulation electrode 64 about a target nerve. Other formats are also acceptable. Moreover, the stimulation electrode 64 can include an array of electrode bodies to deliver a stimulation signal to a target nerve. In some non-limiting embodiments, the stimulation electrode 64 can comprise at least some of substantially the same features and attributes as described within at least U.S. Pat. No. 8,340,785 issued Dec. 25, 2012 and/or U.S. Patent Application Publication No. 2011/0147046 published Jun. 23, 2011 the entire teachings of each of which are incorporated herein by reference in their entireties.

In some examples, the lead body 62 is a generally flexible elongate member having sufficient resilience to enable advancing and maneuvering the lead body 62 subcutaneously to place the stimulation electrode 64 at a desired location adjacent a nerve, such as an airway-patency-related nerve (e.g. hypoglossal nerve, vagus nerve, etc.). In some examples, such as in the case of obstructive sleep apnea, the nerves may include (but are not limited to) the nerve and associated muscles responsible for causing movement of the tongue and related musculature to restore airway patency. In some examples, the nerves may include (but are not limited to) the hypoglossal nerve and the muscles may include (but are not limited to) the genioglossus muscle. In some examples, lead body 62 can have a length sufficient to extend from the IPG assembly 22 implanted in one body location (e.g. pectoral) and to the target stimulation location (e.g. head, neck). Upon generation via the circuitry 32, a stimulation signal is selectively transmitted to the interface block 24 for delivery via the stimulation lead 40 to such nerves.

With non-limiting embodiments in which the interface blocks of the present disclosure are provided as part an IMD, the IMD 20 can incorporate one or more additional components conducive, for example, for treatment of SDB. With these and other embodiments, the systems of the present disclosure can incorporate one or more additional features, such as appropriate programming for delivering a desired therapy, a remote control device, etc. In some examples, the control portion of such systems provides one example implementations of a control portion forming a part of, implementing, and/or managing any one of devices, systems, assemblies, circuitry, managers, engines, functions, parameters, sensors, electrodes, modules, and/or methods, as represented throughout the present disclosure.

In general terms, some example devices of the present disclosure can include a controller that comprises the electronics (e.g., the circuitry 32 such as at least one processor, microprocessor, integrated circuits and logic, etc.) and associated memories or storage devices. The controller is electrically couplable to, and in communication with, a memory to generate control signals to direct operation of at least some the devices, systems, assemblies, circuitry, managers, modules, engines, functions, parameters, sensors, electrodes, and/or methods, as represented throughout the present disclosure (e.g., a software program stored on a storage device, loaded onto the memory, and executed by the electronics assembly). It will be further understood that the controller (or another control portion) may also be employed to operate general functions of the various therapy devices/systems described throughout the present disclosure.

In some non-limiting examples, in response to or based upon commands received via a user interface and/or via machine readable instructions, the controller generates control signals to implement therapy implementation, therapy monitoring, therapy management, and/or management. In some examples, the controller is embodied in a general purpose computing device while in some examples, the controller is incorporated into or associated with at least some of the associated devices, systems, assemblies, circuitry, sensors, electrodes, components of the devices and/or managers, engines, parameters, functions etc. described throughout the present disclosure.

For purposes of the present disclosure, in reference to the controller, with embodiments in which the electronics assembly comprises or includes at least one processor, the term "processor" shall mean a presently developed or future developed processor (or processing resources) or microprocessor that executes sequences of machine readable instructions contained in a memory. In some examples, execution of the sequences of machine readable instructions, such as those provided via the memory cause the processor to perform actions, such as operating the controller to implement sleep disordered breathing (SDS) therapy and related management and/or management and operation of designated physical action sensing, as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by the memory. In some examples, the memory comprises a computer readable tangible medium providing non-volatile storage of the machine readable instructions executable by a process of the controller. In other examples, hard wired circuitry may be used in place of or in combination with machine readable instructions to implement the functions described. For example, the electronics assembly may be embodied as part of at least one application-specific integrated circuit (ASIC), at least one integrated circuit, a microprocessor and ASIC, etc. In at least some examples, the controller is not limited to any specific combination of hardware circuitry and machine readable instructions, nor limited to any particular source for the machine readable instructions executed by the controller.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein.

The invention claimed is:

1. An electronic device comprising:
   an interface block including:
      a flange assembly defining an aperture,
      a feedthrough pin extending through the aperture and defining a leading region opposite a trailing region, wherein the leading and trailing regions are disposed at opposite sides of the flange assembly;
      a printed circuit board assembly including a substrate carrying a circuitry trace and a conductor body electrically coupled to the circuitry trace;
      a reflow solder bond between the trailing region and the conductor body;
      wherein a central axis of the trailing region is substantially parallel with a major plane of the substrate;
      a housing coupled to the flange assembly; and
      electrical circuitry maintained within the housing, the electrical circuitry including an electrical component electrically coupled to the circuitry trace opposite the conductor body.

2. The electronic device of claim 1, wherein the leading region terminates at a first end of the feedthrough pin and the trailing region terminates at a second end of the feedthrough pin, and further wherein a diameter of the feedthrough pin at the second end is greater than a diameter of the feedthrough pin along the leading region.

3. The electronic device of claim 2, wherein the feedthrough pin includes a pin body defining the leading region and a secondary body attached to the pin body to define the trailing region.

4. The electronic device of claim 3, wherein a material of the secondary body differs from a material of the pin body, and further wherein the material of the secondary body is selected to enhance a reliability of the reflow solder bond.

5. The electronic device of claim 1, wherein the feedthrough pin includes a surface coating selected to enhance reliability of the reflow solder bond.

6. The electronic device of claim 1, wherein the trailing region lies on a surface of the substrate.

7. The electronic device of claim 1, wherein the feedthrough pin terminates at a leading end face opposite a trailing end face, and further wherein the trailing region includes the trailing end face, and further wherein at least a portion of the trailing end face does not directly contact the conductor body.

8. The electronic device of claim 1, wherein the feedthrough pin is a cylindrical body defining a leading end face, a trailing end face opposite the leading end face, and a curved side surface, and further wherein the trailing region includes the trailing end face and a portion of the curved side surface, and even further wherein a segment of the curved side surface directly contacts the conductor body.

9. A method of manufacturing an electronic device, the method comprising:
   receiving an interface block including a flange assembly and a feedthrough pin extending through an aperture in the flange assembly, wherein opposing, leading and trailing regions of the feedthrough pin are located at opposite sides of the flange assembly;
   locating the trailing region on a conductor body of a printed circuit board assembly including a substrate carrying the conductor body and a circuitry trace electrically coupled to the conductor body;
   wherein the step of locating includes arranging the interface block relative to the printed circuit board assembly such that a central axis of trailing region is substantially parallel with a major plane of the substrate;
   reflow soldering the trailing region to the conductor body such that the feedthrough pin is electrically coupled to conductor body;
   electrically coupling an electrical component of electrical circuitry to the circuitry trace opposite the conductor body;
   locating the electrical circuitry within a housing; and
   mounting the interface block to the housing.

10. The method of claim 9, wherein the step of reflow soldering includes:
    applying a solder paste to at least one of the trailing region and the conductor body;
    heating the solder paste in an oven to a molten state; and
    cooling the molten solder paste to a hardened state.

11. The method of claim 9, wherein the step of locating the trailing region includes abutting the trailing region against a surface the substrate.

12. The method of claim 9, wherein prior to the step of receiving, the method further comprising:
    joining a secondary body to a pin body to form the feedthrough pin.

13. The method of claim 12, wherein the step of joining includes at least one of welding, solder reflowing, crimping, and swaging the secondary body to the pin body.

14. The method of claim 9, wherein the flange assembly includes an insulator body, and further wherein the step of mounting the interface block to the housing includes a step selected from the group consisting of:
    joining the insulator body directly to the housing; and
    joining a flange body of the flange assembly to the housing, the flange body maintaining the insulator body.

15. The method of claim 9, wherein the step of locating the trailing region on the conductor body includes supporting the leading region of the feedthrough pin on a first support block.

16. The method of claim 9, wherein the feedthrough pin terminates at a leading end face opposite a trailing end face, and further wherein the trailing region includes the trailing end face, and further wherein the step of locating the trailing region on the conductor body includes the trailing end face projecting away from the conductor body.

17. The method of claim 9, wherein the feedthrough pin is a cylindrical body terminating at a leading end face and at a trailing end face opposite the leading end face, an exterior of the cylindrical body further defining a curved side surface from the leading end face to the trailing end face, and further wherein the step of locating the trailing region on the conductor body includes a segment of the curved side surface directly in contact with the conductor body.

* * * * *